US008003615B2

(12) United States Patent
Sakamoto et al.

(10) Patent No.: US 8,003,615 B2
(45) Date of Patent: Aug. 23, 2011

(54) STABLE VITAMIN B6 DERIVATIVE

(75) Inventors: Keiji Sakamoto, Takaoka (JP); Koichi Wada, Toyama (JP); Hajime Ito, Tonami (JP); Nobuhiro Take, Himi (JP); Hiroshi Morimoto, Imizu (JP); Fumio Maniwa, Kashiwa (JP); Yukiko Shimmoto, Kawaguchi (JP)

(73) Assignee: Daiichi Fine Chemical Co., Ltd., Toyama (JP)

( * ) Notice: Subject to any disclaimer, the term of this patent is extended or adjusted under 35 U.S.C. 154(b) by 0 days.

(21) Appl. No.: 10/573,973

(22) PCT Filed: Sep. 30, 2004

(86) PCT No.: PCT/JP2004/014768
§ 371 (c)(1), (2), (4) Date: Feb. 22, 2007

(87) PCT Pub. No.: WO2005/033123
PCT Pub. Date: Apr. 14, 2005

(65) Prior Publication Data
US 2007/0148108 A1 Jun. 28, 2007

(30) Foreign Application Priority Data

Oct. 1, 2003 (JP) .................................. 2003-342918
May 26, 2004 (JP) .................................. 2004-155624

(51) Int. Cl.
*A61K 31/70* (2006.01)
*A61K 31/7028* (2006.01)
*A61K 31/7042* (2006.01)
*A61K 31/7052* (2006.01)
*A61K 31/706* (2006.01)

(52) U.S. Cl. ............ 514/27; 514/25; 536/4.1; 536/17.4; 536/17.9; 536/18.5

(58) Field of Classification Search ............. 514/27, 514/25; 536/4.1, 17.4, 17.9, 18.5
See application file for complete search history.

(56) References Cited

U.S. PATENT DOCUMENTS 6,685,970 B1    2/2004   Takahashi et al.

FOREIGN PATENT DOCUMENTS

| FR | 2349330 A | * 12/1977 |
|----|-----------|-----------|
| JP | 59-199674 | 11/1984 |
| JP | 60-188306 | 9/1985 |
| JP | 5-17355 | 1/1993 |
| JP | 7-206664 | 8/1995 |
| JP | 2001-158739 | 6/2001 |
| JP | 2001-342110 | 12/2001 |
| JP | 2002-265316 | 9/2002 |
| JP | 2002-265368 | 9/2002 |
| JP | 2003-206279 | 7/2003 |
| JP | 2003-535880 | 12/2003 |
| JP | 2004031370 | 3/2004 |
| JP | 2004-357591 | 12/2004 |
| JP | 2008-013578 | 1/2008 |
| WO | 01/97760 A1 | 12/2001 |
| WO | 02/072039 | 9/2002 |

OTHER PUBLICATIONS

Trumbo et al. (Journal of Nutrition (1988), 118 (2), 170-5) (Abstract Sent).*
Ogata et al. (The Journal of Vitaminology 15, 160-166 (1969)).*
Abstract of JP 20002-265316, Sep. 18, 2002.*
Shionogi and Co., Ltd. (FR 2196793 A2), Mar. 22, 1974 (Abstract sent).*
Mineura et al. (Nippon Nogei Kagaku Kaishi (1972), 46(3), 111-18 (Abstract sent).*
Abstract of FR 2349330 A; Dec. 30, 1977.*
Nobuyasu Mizuno and Michiyo Fujimoto, "Hydrolysis of Pyridoxine Monooctanoates", Vitamins, vol. 49, pp. 395-401, 1975.
Dorothea Heyl et al., "Phosphates of the Vitamin B6 Group I. The Structure of Codecarboxylase", J. Am. Chem. Soc., vol. 73, pp. 3430-3439, 1951.
Jikken-Kagaku-Koza (Lecture of Experimental chemistry) vol. 26, 4th edition, Organic sysnthesis VIII (edited by Chemical Society of Japan, Maruzen, 1992).
Fundamentals and Experiments of Peptide Synthesis, Maruzen Co., Ltd., 1985.
Stephen P. Coburn et al., "Identification of Pyridoxine 3-Sulfate, Pyridoxal 3-Sulfate, and N-Methylpyridoxine as Major Urinary Metabolites of Vitamin B6 in Domestic Cats", The Journal of Biological Chemistry, vol. 262, No. 6, pp. 2642-2644, 1987.
Donald L. Bissett et al., "An Animal Model of Solar-Aged Skin: Historical, Physical, and Visible Changes in UV-Irradiated Hairless Mouse Skin", Photochemistry and Photobiology, vol. 46, No. 3, pp. 367-378, 1987.

(Continued)

*Primary Examiner* — Shaojia Anna Jiang
*Assistant Examiner* — Michael C Henry
(74) *Attorney, Agent, or Firm* — Greenblum & Bernstein, P.L.C.

(57) ABSTRACT

A compound represented by the following general formula (I) or a salt thereof:

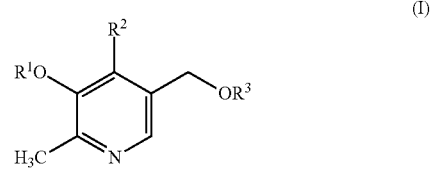

(I)

wherein $R^1$ represents a glycosyl group, a phosphate group, or a cyclic phosphate group bound to $R^2$; $R^2$ represents $-CH_2OH$, $-CHO$, $-CH_2NH_2$, $-CH_2$-amino acid residue, or $-CH_2-OPO_2H$; and $R^3$ represents hydrogen atom, or $-PO_3H_2$, and a composition for cosmetics, medicaments, foodstuffs, and/or feeds containing the aforementioned compound or a salt thereof.

8 Claims, 12 Drawing Sheets

OTHER PUBLICATIONS

Ernst Graf et al., "Iron-catalyzed Hydroxyl Radical Formation", Journal of Biological Chemistry, vol. 259, No. 6, pp. 3620-3624, 1984.
Beth Anne Jurkiewicz and Garry R. Buettner, "Ultraviolet Light-Induced Free Radical Formation In Skin: An Electron Paramagnetic Resonance Study", Photochemistry and Photobiology, vol, 59, pp. 1-4, 1994.
English Language Abstract of JP 59-199674, Nov. 12, 1984.
English Language Abstract of JP 2004-357591, Dec. 24, 2004.
English Language Abstract of JP 2004031370, Mar. 25, 2004.
English Language Abstract of JP 2001-158739, Jun. 12, 2001.
Gilbert et al., "Pyridoxine-5'-β-D-Glucoside Affects the Metabolic Utilization of Pyridoxine in Rats," Journal of Nutrition, vol. 122, No. 4, pp. 1029-1035, 1992.
Tadera et al., "A Particulate Glucosyltransferase Catalyzing the Formation of 5'-O-(β-D-Glucopyranosyl)pyridoxine from Pyridoxine: The Occurrence in the Seedlings of *Pisum sativum* L.," Journal of Nutritional Science and Vitaminology, vol. 25, No. 4, pp. 347-350, 1979.
Gregory et al., "Identification and Quantification of Pyridoxine-β-Glucoside as a Major Form of Vitamin $B_6$ in Plant-Derived Foods," Journal of Agricultural Food Chemistry, vol. 35, pp. 76-82, 1987.
Gregory et al., "Preparation of Nonlabeled, Tritiated, and Deuterated Pyridoxine 5'-β-D-Glucoside and Assay of Pyridoxine 5'-β-D-Glucoside Hydrolase," in Methods of Enzymology, vol. 280 (Vitamins and Coenzyme Part J), pp. 58-71, 1997.
Iyakuhin Gousei Kagaku, Jun. 20, 1980, pp. 433-435.
Mineura et al. "Studies on the Production of Pyridoxal Phosphate Part I. Photooxidation of Pyridoxine-5'-phosphate and Pyridoxine-4'5'-cyclicphosphate in the Presence of Flavin Compounds" *Nippon Nogei Kagaku Kaishi* 46(3): 103-110,1972.
Chemical Structure of RN 14141-47-0, downloaded Jan. 14, 2010.
Vinh Pham et al., "Design and Synthesis of Novel Pyridoxine 5'-Phosphonates as potential Antiischemic Agents", J. Med. Chem., vol. 46, pp. 3680-3687, 2003.
English Language Abstract of JP 2002-265368., Sep. 18, 2002.
Koichi Ogata et al., "Studies on Transglycosidation to Vitamin B6 by Microorganisms", The Journal of Vitaminology, vol. 15, pp. 160-166, 1969.
Yukio Suzuki et al., "Enzymatic Preparation of Pyridoxine 4'-and 5'-α-D-Glucosides", Methods in Enzymology, vol. 280, pp. 66-71, 1997.
English Language Abstract of JP 2002-265316, Sep. 18, 2002.
Fusako Kawai et al., "Properties of Pyridoxine Glucoside", The Journal of Vitaminology, vol. 17, pp. 121-124, 1971.
Masahide Shiroshi and Akira Hayakawa, "Effects of Sunlight Irradiation on Vitamin $B_6$ Relating compounds", Vitamins, vol. 22, pp. 138-141, 1961.
English Language Abstract of JP 7-206664., Aug. 8, 1995.
Shinichi Takasaki and Hiroaki Yoshida, Katei-yaku Kenkyu (Home Remedy Research)., vol. 54, No.5, pp. 54-58, 1986.
English Language Abstract of JP 5-17355., Jan. 26, 1993.
Fragrance Journal, vol. 17, No. 3, pp. 96-100, 1989.
Protective Groups in Organic Syntheses, John Wiley & Sons, Inc., 1999.
Handbook of Regents for Organic Synthesis, four volumes in total, John Wiley & Sons, Inc., 1999.
W. Korytnyk and B. Paul, "Acyl Migration and Selective Esterification in Pyridoxol", J. Org. Chem., vol. 32, pp. 3791-3796, 1967.
Higuchi et al., Chem. Pharm. Bull. 40(3) 829-831 (1992).
Office Action in Japanese Application 2005-514496 date Nov. 24, 2010.
Mineura et al., Nippon Nogei Kagaku Kaishi, vol. 46, No. 3, pp. 111-118, 1972, accompanied by an English translation.

\* cited by examiner

STABLE VITAMIN B6 DERIVATIVE

TECHNICAL FIELD

The present invention relates to a stable vitamin B6 derivative.

BACKGROUND ART

Each of pyridoxine, pyridoxal, and pyridoxamine is a substance having vitamin B6 action, and referred to as a class of vitamin B6 together with each 5'-phosphate thereof, i.e., pyridoxine 5'-phosphate, pyridoxal 5'-phosphate, and pyridoxamine 5'-phosphate. These compounds are metabolized to give pyridoxal 5'-phosphate in vivo, and play an important role as a coenzyme for enzymes involved in amino acid metabolism.

It is known that pyridoxine and hydrochloride thereof are extremely unstable to light, and similarly, pyridoxal, pyridoxamine, and pyridoxal 5'-phosphate are also very unstable to light. For this reason, it is desired to provide a compound of the vitamin B6 class that has improved light stability.

Several vitamin B6 glycosides in which vitamin B6 is glycosylated have been reported. For example, pyridoxine 5'-β-D-glucoside exists in plant bodies. However, light stability thereof has not been reported. Vitamin B6 glycosides glycosylated at the 4'- or 5'-position (pyridoxine 4'-α-D-glucoside, pyridoxine 5'-α-D-glucoside) were enzymatically synthesized (for example, J. Vitaminol., 15, pp. 160-166, 1969; and Methods in Enzymology, 280, pp. 66-71, 1997). As for the stability of pyridoxine 4'-α-D-glucoside, and pyridoxine 5'-α-D-glucoside, it has been reported that these substances have superior long term stability at 50° C. in pharmaceutical preparations compared with pyridoxine hydrochloride (for example, Japanese Patent Unexamined Publication (KOKAI) Nos. 2002-265316 and 2002-265368). As for light stability, it has been reported that light stability of a mixture of pyridoxine 4'-α-D-glucoside and pyridoxine 5'-α-D-glucoside is improved compared with pyridoxine hydrochloride under an ultraviolet lamp irradiation test (for example, J. Vitaminol., 17, pp. 121-124, 1971). However, the reported stability is not sufficient for practical applications. No compound has been reported so far in which vitamin B6 is glycosylated at the 3-position and esterified into phosphoric acid ester.

It is known that light stability of vitamin B6 is improved by addition of boric acid (Vitamins, 22, pp. 138-141, 1961) or addition of a sugar alcohol (Japanese Patent Unexamined Publication (KOKAI) No. 07-206664). However, the effect is not satisfactory, and moreover, a problem arises that the use is limited by the addition of boric acid or a sugar alcohol.

It is known that when vitamin B6 is mixed with other class of vitamins, decomposition of the other vitamins may sometimes be accelerated. For example, it has been reported that when calcium pantothenate and vitamin B6 are mixed and stored at 40° C. under 75% RH, decomposition of calcium pantothenate is accelerated (Katei-yaku Kenkyu (Home Remedy Research), 54(5), pp. 54-58, 1986). It is known that in an aqueous solution added with boric acid, both of vitamin B6 and pantothenic acid can stably exist (Japanese Patent Unexamined Publication (KOKAI) No. 05-17355). However, the effect is not satisfactory, and a problem arises that the use is limited by the addition of boric acid.

Vitamin B6 is a vitamin that plays an important role for protein metabolism in vivo, and also acts as a coenzyme in metabolism of fats. Shortage of vitamin causes skin inflammation, swelling, psilosis and the like (Fragrance Journal, 17 (3), 96-100 (1986); Japanese Patent Unexamined Publication (KOKAI) No. 2002-265368). As dermal external preparations, external preparations added with a vitamin B6 derivative such as pyridoxine hydrochloride have conventionally been used for relief of skin roughness, pimple, sun tanning, and hot flush by snow burning, therapeutic and prophylactic treatments of itching due to inflammation, dandruff due to seborrhea sicca and the like. However, vitamin B6 derivatives conventionally used have problems that they have poor light stability, and decomposition products thereof cause skin irritation and the like. They also have a problem that sufficient effects as vitamin B6 cannot be obtained when they are added and used in skin external preparations.

DISCLOSURE OF THE INVENTION

The instability of vitamin B6 and derivatives thereof, especially the instability to light, is an obstacle for practical use of these substances. If a vitamin B6 derivative that is stable to light can be provided, the derivative will successfully expand utilities thereof. Therefore, an object of the present invention is to provide a stable vitamin B6 derivative. In particular, the object of the present invention is to provide a vitamin B6 derivative having improved stability against light.

The inventors of the present invention conducted various researches to achieve the aforementioned object. As a result, they found that a vitamin B6 derivative having a particular structure in which vitamin B6 was glycosylated or made into phosphoric acid or sulfuric acid ester (hereinafter also referred to as a "vitamin B6 derivative") at the 3-position had superior stability, and especially the stability thereof against light was remarkably improved. The inventors of the present invention further conducted researches, and found a novel compound useful as an intermediate for manufacture of the aforementioned vitamin B6 derivative, and an efficient method for producing the aforementioned vitamin B6 derivative using the aforementioned intermediate. The inventors of the present invention also found that the aforementioned vitamin B6 derivative was stably maintained in a composition such as medicaments, foodstuffs, feeds, cosmetics and the like to exhibit superior effects, and the derivative gave no influence on the stability of other vitamins in the composition. They further found that the aforementioned vitamin B6 derivative had remarkable advantageous effects, in particular, whitening effect, anti-aging effect, wrinkle suppressing effect and the like. The present invention was achieved on the basis of the aforementioned findings.

The present invention thus provides a compound represented by the following general formula (I) or a salt thereof:

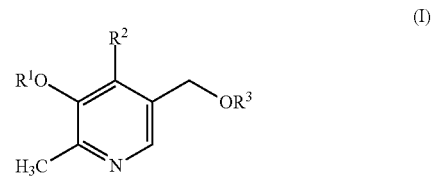

(I)

wherein $R^1$ represents a glycosyl group, a phosphate group, or a cyclic phosphate group bound to $R^2$; $R^2$ represents —$CH_2OH$, —CHO, —$CH_2NH_2$, —$CH_2$-amino acid residue, or —$CH_2$—$OPO_2H$; and $R^3$ represents hydrogen atom, or —$PO_{31}$-12.

According to another embodiment of the present invention, there is provided a compound represented by the following general formula (IV) or a salt thereof

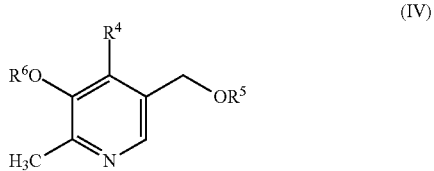

(IV)

wherein $R^4$ represents —CH$_2$OH, —CHO, or —CH$_2$NH$_2$, or represents —CH$_2$OH, —CHO, or —CH$_2$NH$_2$ which is protected with a protective group; $R^6$ represents hydrogen atom, a protective group of hydroxyl group, a phosphate group, or a protected phosphate group; and $R^6$ represents a glycosyl group which may have a protective group, or a phosphate group which may have a protective group, which is useful as an intermediate for the manufacture of the compound represented by the aforementioned general formula (I).

According to another embodiment of the present invention, there is provided a method for preparing a compound represented by the aforementioned general formula (I) or a salt thereof, which comprises the step of reacting a compound represented by the following general formula (II) or a salt thereof

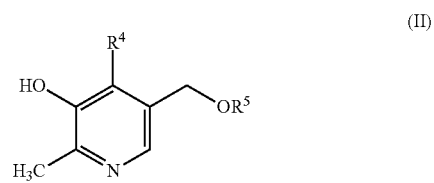

(II)

wherein $R^4$ represents —CH$_2$OH, —CHO, or —CH$_2$NH$_2$, or represents —CH$_2$OH, —CHO, or —CH$_2$NH$_2$ which is protected with a protective group; and $R^6$ represents hydrogen atom, a protective group of hydroxyl group, a phosphate group, or a protected phosphate group, with a compound represented by the following general formula (III):

R$^6$—X    (III)

wherein $R^6$ represents a glycosyl group which may have a protective group, and X represents a leaving group, to obtain the compound represented by the aforementioned general formula (IV), and if necessary, the step of deprotecting the compound represented by the aforementioned general formula (IV).

The present invention also provides a composition for cosmetics, medicaments, foodstuffs, and/or feeds which comprises a compound represented by the following general formula (V) or a salt thereof:

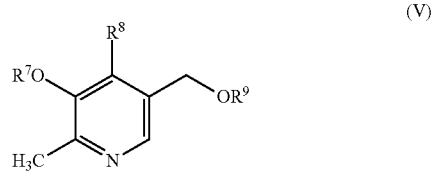

(V)

wherein $R^7$ represents a glycosyl group, a phosphate group, a sulfate group, or a cyclic phosphate group bound to $R^8$; $R^8$ represents —CH$_2$OH, —CHO, —CH$_2$NH$_2$, —CH$_2$-amino acid residue, or —CH$_2$—OPO$_2$H; and $R^9$ represents hydrogen atom, or —PO$_3$H$_2$.

The present invention also provide a method for stabilizing a vitamin in a composition for cosmetics, medicaments, foodstuffs, and/or feeds by adding the compound represented by the general formula (V) or a salt thereof to the composition, and a composition for cosmetics, medicaments, foodstuffs, and/or feeds containing the compound represented by the general formula (V) or a salt thereof and at least one kind of vitamin, wherein stability of the vitamin is improved.

In addition to the aforementioned inventions, the present invention further provides the aforementioned composition for cosmetics, which is a whitening agent, an anti-aging agent, and/or an agent for suppressing wrinkle formation by exposure to ultraviolet light; a cosmetic composition comprising (A) the compound represented by the general formula (V), and (B) one or more kinds of substances selected from the group consisting of a whitening agent, an antioxidant, an anti-inflammatory agent, a blood circulation accelerator, a cell activation agent, and an ultraviolet absorber, which is used as a whitening agent, an anti-aging agent, and/or an agent for suppressing wrinkle formation by exposure to ultraviolet light; and a whitening agent containing (A) the compound represented by the general formula (V), and (B) arbutin.

Figure 11:
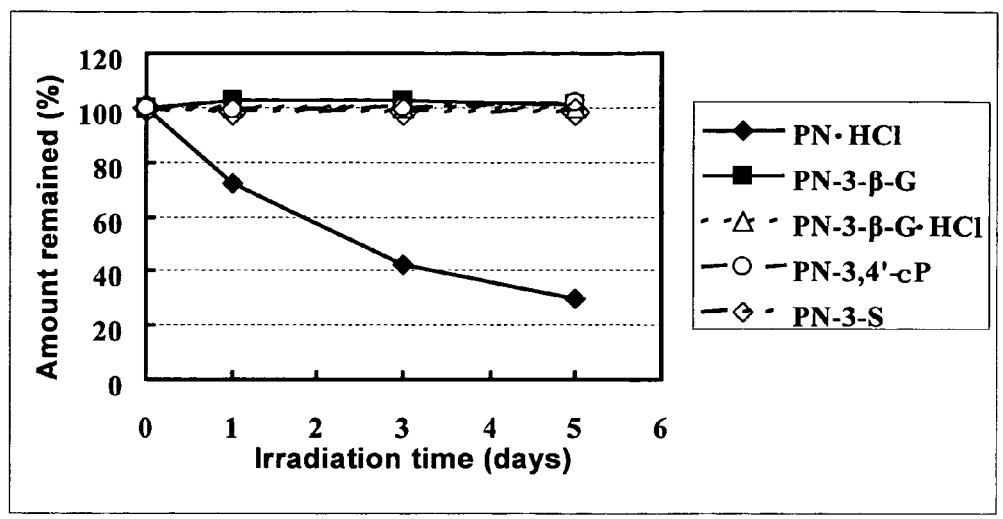

FIG. 11 shows light stability of the compounds of the present invention in a lotion. PN.HCl represents pyridoxine hydrochloride, PN-3-β-G represents pyridoxine 3-β-D-glucoside, PN-3-β-G.HCl represents pyridoxine 3-β-D-glucoside hydrochloride, PN-3,4'-cP represents pyridoxine 3,4'-cyclic sodium phosphate, and PN-3-S represents pyridoxine 3-sodium sulfate.

Figure 12:
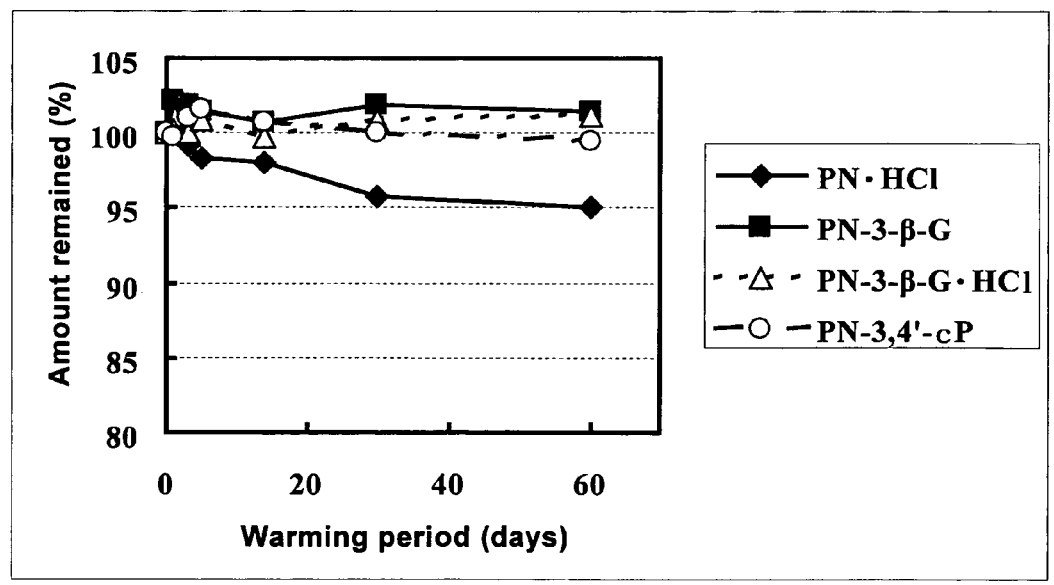

FIG. 12 represents thermal stability of the compounds of the present invention in a lotion. PN.HCl represents pyridoxine hydrochloride, PN-3-β-G represents pyridoxine 3-α-D-glucoside, PN-3-β-G.HCl represents pyridoxine 3-(3-D-glucoside hydrochloride, and PN-3,4'-cP represents pyridoxine 3,4'-cyclic sodium phosphate.

Figure 13:
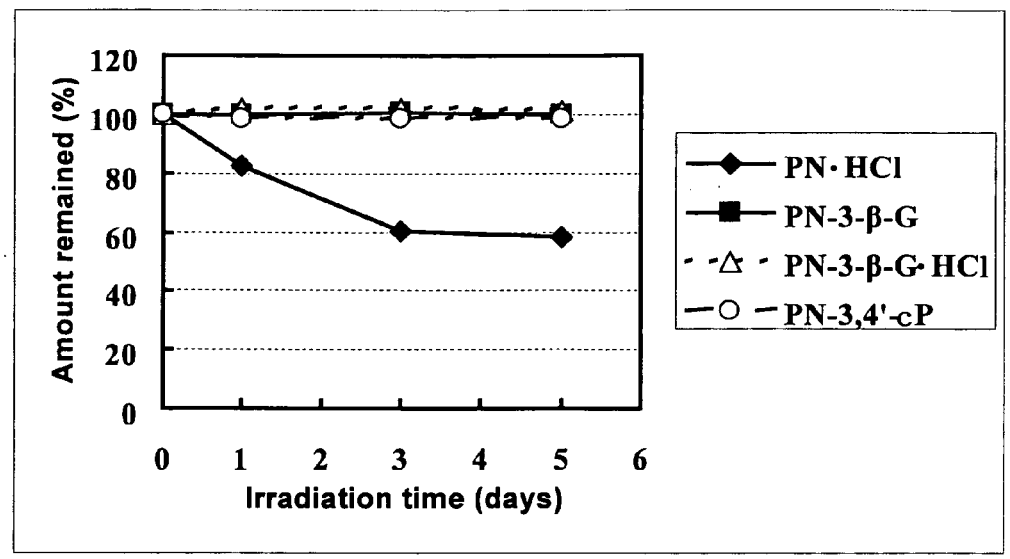

FIG. 13 shows light stability of the compounds of the present invention in a shampoo. PN.HCl represents pyridoxine hydrochloride, PN-3-β-G represents pyridoxine 3-β-D-glucoside, PN-3-β-G.HCl represents pyridoxine 3-β-D-glucoside hydrochloride, and PN-3,4'-cP represents pyridoxine 3,4'-cyclic sodium phosphate.

Figure 14:
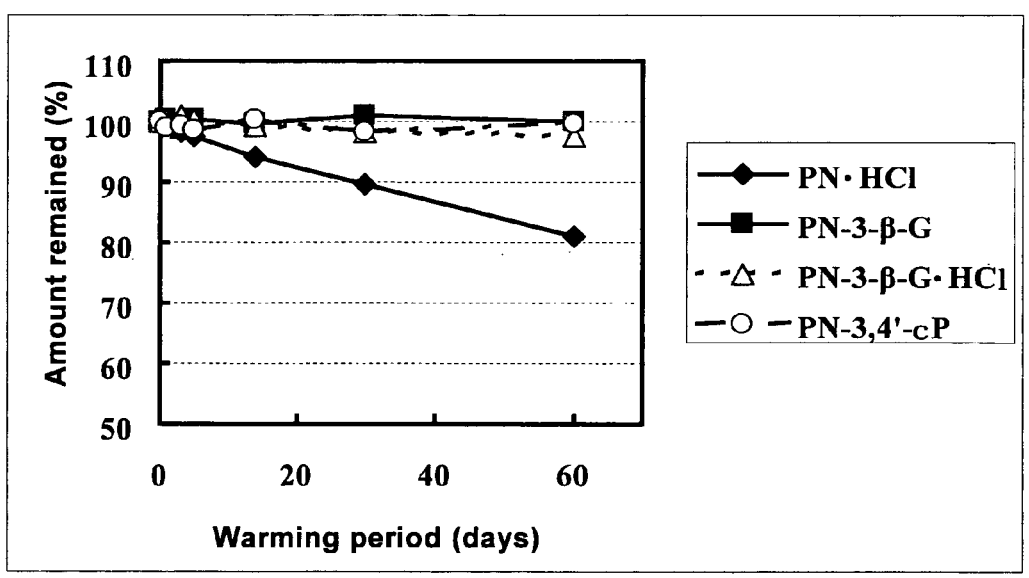

FIG. 14 shows thermal stability of the compounds of the present invention in a shampoo. PN.HCl represents pyridoxine hydrochloride, PN-3-β-G represents pyridoxine 3-β-D-glucoside, PN-3-β-G.HCl represents pyridoxine 3-β-D-glucoside hydrochloride, and PN-3,4'-cP represents pyridoxine 3,4'-cyclic sodium phosphate.

Figure 15:
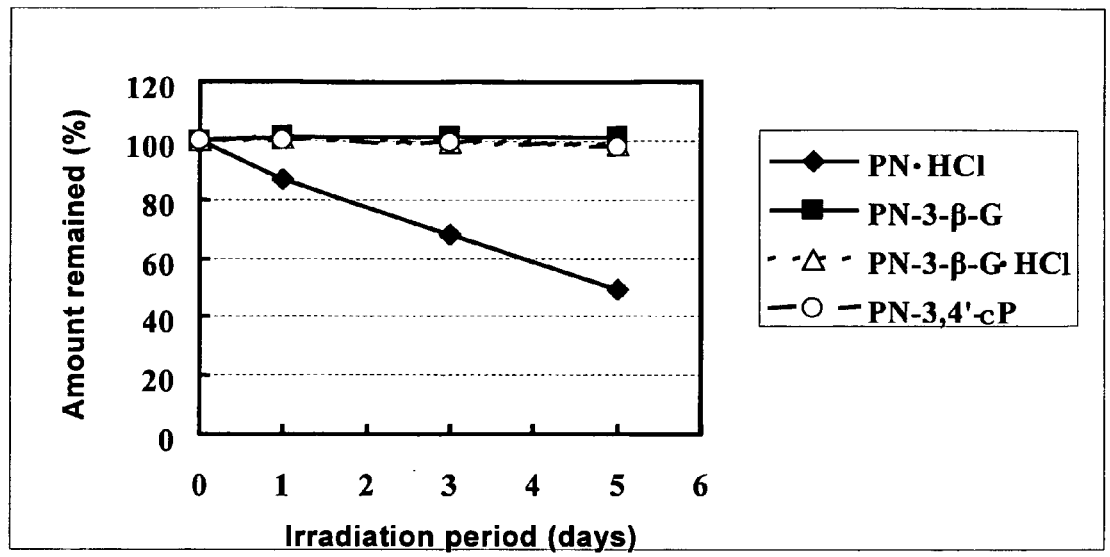

FIG. 15 shows light stability of the compounds of the present invention in an eye lotion. PN.HCl represents pyridoxine hydrochloride, PN-3-β-G represents pyridoxine 3-β-D-glucoside, PN-3-β-G.HCl represents pyridoxine 3-β-D-glucoside hydrochloride, and PN-3,4'-cP represents pyridoxine 3,4'-cyclic sodium phosphate.

Figure 16:
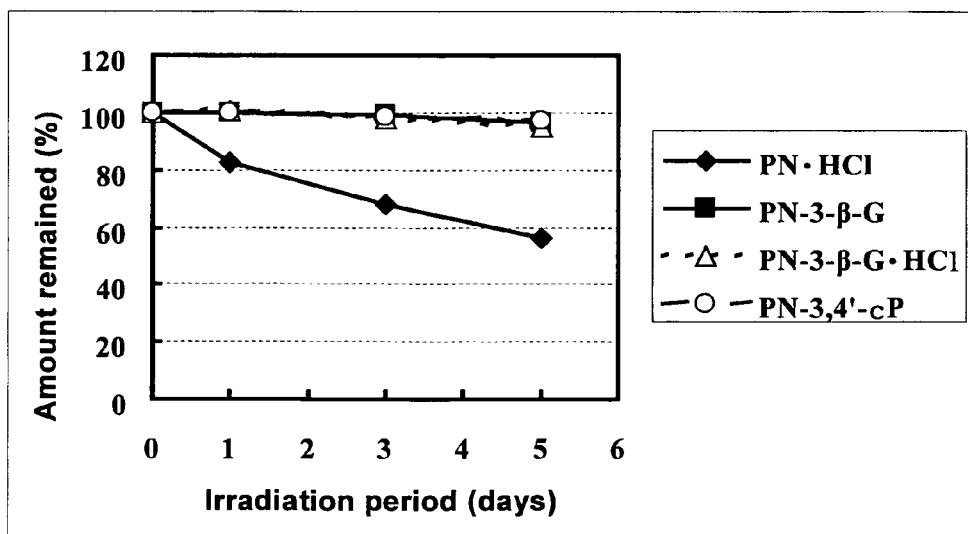

FIG. 16 shows light stability of the compounds of the present invention in a drinking water. PN.HCl represents pyridoxine hydrochloride, PN-3-β-G represents pyridoxine 3-β-D-glucoside, PN-3-β-G.HCl represents pyridoxine 3-β-D-glucoside hydrochloride, and PN-3,4'-cP represents pyridoxine 3,4'-cyclic sodium phosphate.

Figure 17:
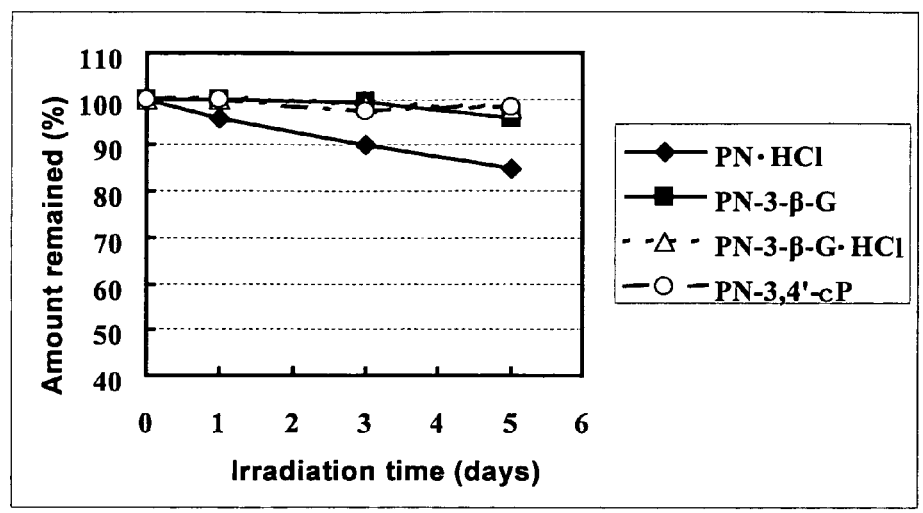

FIG. 17 shows light stability of the compounds of the present invention in a dog food. PN.HCl represents pyridoxine hydrochloride, PN-3-β-G represents pyridoxine 3-β-D-glucoside, PN-3-β-G.HCl represents pyridoxine 3-β-D-glucoside hydrochloride, and PN-3,4'-cP represents pyridoxine 3,4'-cyclic sodium phosphate.

Figure 18:
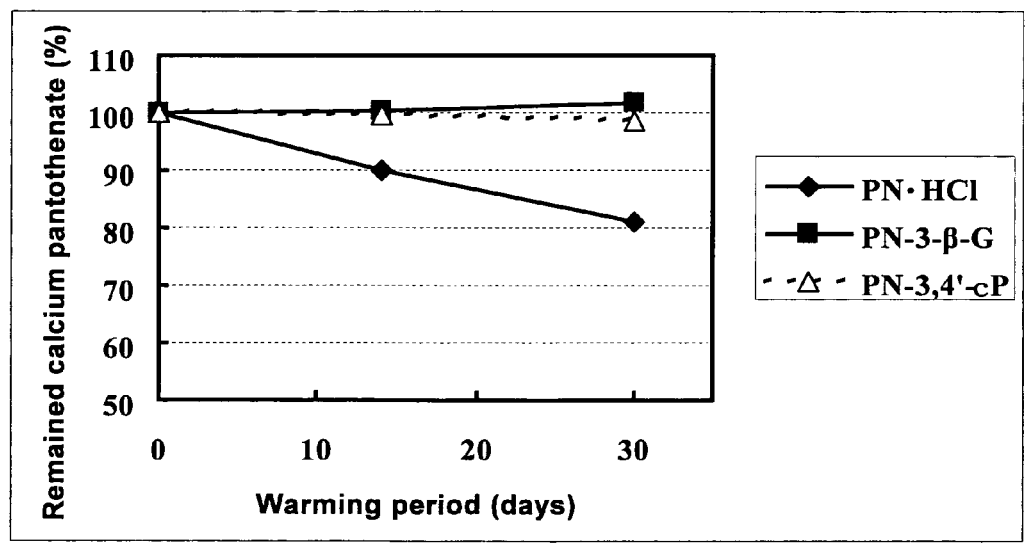

FIG. 18 shows stability of calcium pantothenate mixed with the compounds of the present invention. In the drawing, PN.HCl represents the remaining amount of calcium pantothenate mixed with pyridoxine hydrochloride, PN-3-(3-G represents the remaining amount of calcium pantothenate mixed with pyridoxine 3-β-D-glucoside, and PN-3,4'-cP represents the remaining amount of calcium pantothenate mixed with pyridoxine 3,4'-cyclic sodium phosphate.

Figure 19:
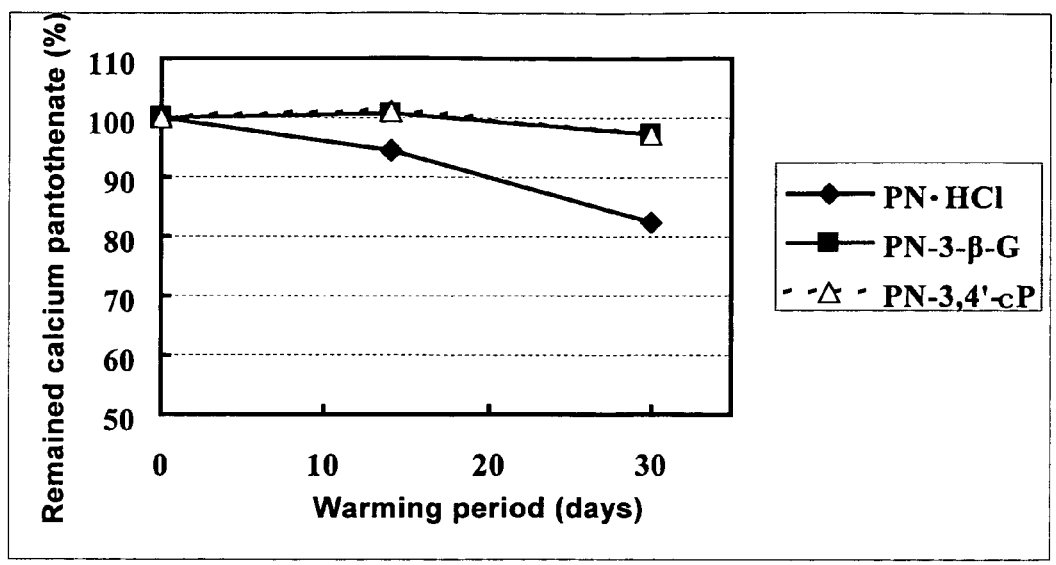

FIG. 19 shows stability of calcium pantothenate mixed with the compounds of the present invention in an aqueous solution. In the drawing, PN.HCl represents the remaining amount of calcium pantothenate mixed with pyridoxine hydrochloride, PN-3-β-G represents the remaining amount of calcium pantothenate mixed with pyridoxine 3-β-D-glucoside, and PN-3,4'-cP represents the remaining amount of calcium pantothenate mixed with pyridoxine 3,4'-cyclic sodium phosphate.

Figure 20:
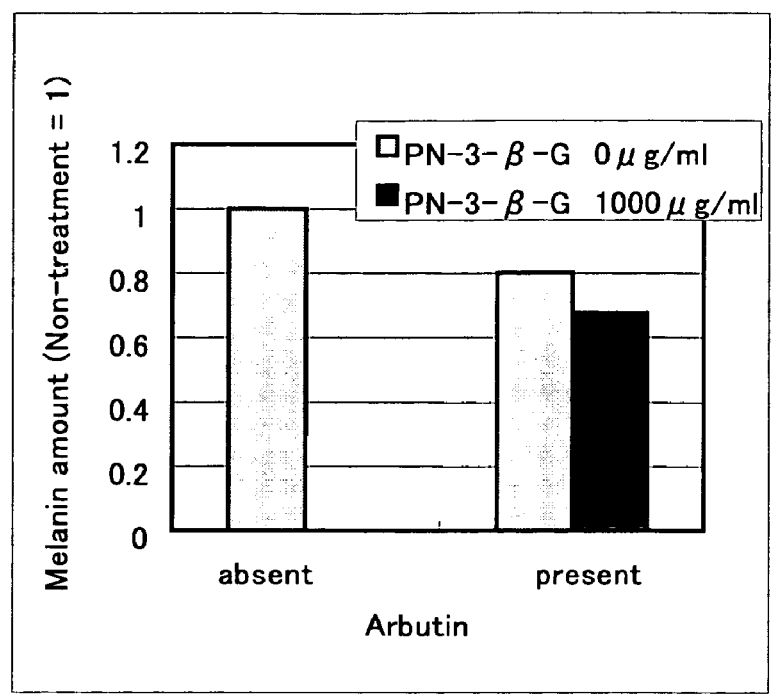

FIG. 20 shows synergistic whitening effect of a composition comprising the compound of the present invention and arbutin. PN-3-β-G represents pyridoxine 3-β-D-glucoside.

Figure 21:
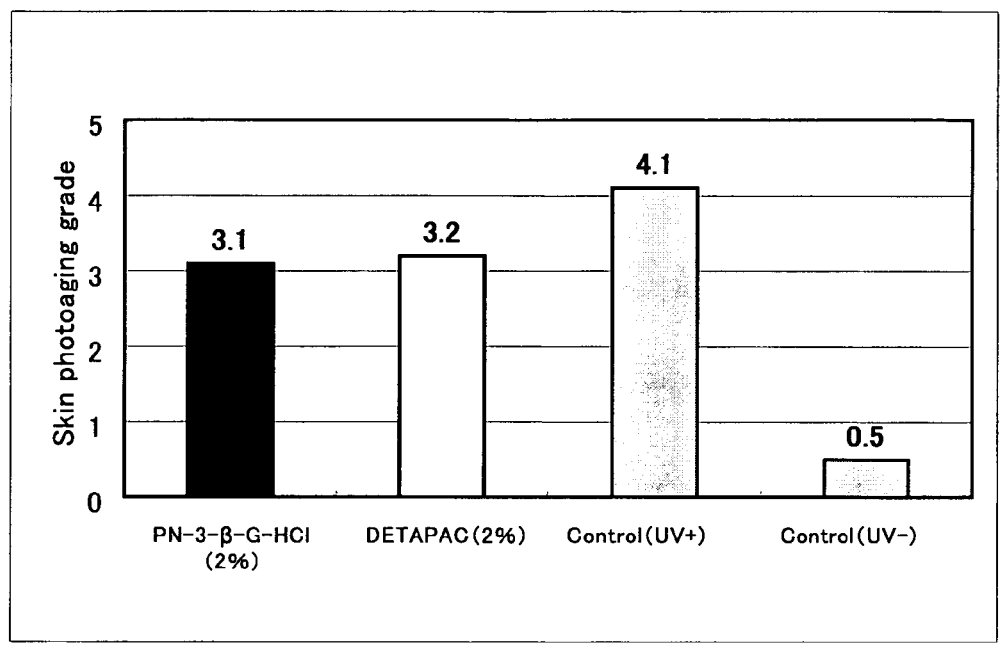

FIG. 21 shows appearance-based graded evaluation of photoaging of skin (after ten weeks) using the compound of the present invention. PN-3-β-G.HCl represents pyridoxine 3-β-D-glucoside hydrochloride, and DETAPAC represents a pentasodium diethylenetriaminepentaacetate solution.

BEST MODE FOR CARRYING OUT THE INVENTION $R^1$ represents a glycosyl group, a phosphate group, or a cyclic phosphate group bound to $R^2$. In the specification, the term "glycosyl group" means a residue obtained by removing hydroxyl group of the 1-position of a saccharide compound (2-position for fructose). The anomer type of the ether linkage between the glycosyl group represented by $R^1$ and the pyridine ring may be either α or β type, or a mixture thereof. The type of the saccharide compound constituting the glycosyl group is not particularly limited, and may be, for example, a monosaccharide, or any of oligosaccharides including disaccharides, trisaccharides, tetrasaccharides, and larger oligosaccharides. The stereochemistry of the saccharide compound may be any of D-, L-, or a mixture thereof. Examples of the saccharide compound constituting the glycosyl group include, for example, D-glucose, L-glucose, D-galactose, L-galactose, D-mannose, L-mannose, D-fructose, L-fructose, D-ribose, L-ribose, D-xylose, L-xylose, D-arabinose, L-arabinose, D-talose, L-talose, D-lyxose, L-lyxose, D-allose, L-allose, D-altrose, L-altrose, D-gulose, L-gulose, D-idose, L-idose, D-quinovose, L-quinovose, D-rhamnose, L-rhamnose, D-fucose, L-fucose, maltose, cellobiose, lactose, maltotriose and the like. Among them, D-glucose and D-galactose are preferred.

The phosphate group represented by $R^1$ may be any of linear esters such as monophosphate, pyrophosphate, and tripolyphosphate, cyclic esters formed with monophosphate, pyrophosphate, tripolyphosphate, or the like of $R^2$, or a mixture of the both.

$R^2$ represents —$CH_2OH$, —CHO, —$CH_2NH_2$, —$CH_2$-amino acid residue, or —$CH_2$—$OPO_2H$. The —$CH_2$-amino acid residue represented by $R^2$ means a group consisting of an amino acid of which amino terminus is bound to —$CH_2$—. When an asymmetric carbon atom of an amino acid exists, the compound may be either an optically active substance or a racemate. Examples of the amino acid compound constituting the amino acid group include, for example, acidic amino acids such as glutamic acid, aspartic acid, cysteic acid, and homocysteic acid, neutral amino acids such as glycine, alanine, valine, leucine, isoleucine, phenylalanine, tryptophan, threonine, serine, homoserine, tyrosine, cysteine, methionine, asparagine, and glutamine, and basic amino acids such as lysine, ornithine, arginine, and histidine. Among them, L-serine is preferred.

The protective groups in $R^4$, $R^5$, and $R^6$ can be suitably chosen by those skilled in the art. For example, protective groups suitable for hydroxyl group, amino group, aldehyde group and the like, and introduction or elimination methods for these groups are described in, for example, Theodora W. Green ed., "Protective Groups in Organic Syntheses", John Wiley & Sons, Inc., 1999; "Handbook of Regents for Organic Synthesis", four volumes in total, John Wiley & Sons, Inc., 1999) and the like. Therefore, those skilled in the art can easily choose an appropriate protective group, and perform introduction and elimination of the protective group.

The compounds represented by the aforementioned general formula (I) or (IV) can form a salt. Examples of pharmacologically acceptable salts include, for example, mineral acid salts such as hydrochloride, hydrobromide, sulfate, nitrate, and phosphate, organic acid salt such as methanesulfonate, benzenesulfonate, para-toluenesulfonate, acetate, propionate, tartrate, fumarate, maleate, malate, oxalate, succinate, citrate, benzoate, mandelate, cinnamate, and lactate. When an acidic group exists, examples of the salts include, for example, metal salts such as lithium salt, sodium salt, potassium salt, magnesium salt, and calcium salt, and ammonium salts such as ammonium salt, methylammonium salt, dimethylammonium salt, trimethylammonium salt, and dicyclohexylammonium salt. They may form a salt with an amino acid such as glycine.

The compounds represented by the aforementioned general formula (I) or (IV) may also exist as a hydrate or a solvate. The compounds represented by the aforementioned general formula (I) or (IV) have one or more asymmetric carbons, and accordingly, they may exist as a stereoisomer such as an optically active substance and a diastereomer. Any of stereoisomers in a pure form, arbitrary mixtures of optical enantiomers or diastereomers, racemates and the like fall within the scope of the present invention.

Preferred examples of the compounds of the present invention represented by the aforementioned general formula (I) include, for example, pyridoxine 3-β-glucoside, pyridoxine 3-α-glucoside, pyridoxamine 3-β-glucoside, pyridoxamine 3-α-glucoside, pyridoxal 3-β-glucoside, pyridoxal 3-α-glucoside, pyridoxine 3-β-galactoside, pyridoxine 3-α-galactoside, N-(4-pyridoxylmethylene)-L-serine 3-β-glucoside, N-(4-pyridoxylmethylene)-L-serine 3-α-glucoside, pyridoxine 3-phosphate, pyridoxine 3,4'-cyclic phosphate, N-(4-pyridoxylmethylene)-L-serine 3-phosphate and the like. Preferred examples also include D-isomers of these compounds. However, the compounds of the present invention are not limited to these examples.

The glycoside compounds of the present invention represented by the general formula (I) can be prepared according to, for example, the following reaction scheme. $R^1$, $R^2$, $R^3$, $R^4$, $R^5$, $R^6$, and X in the formula have the same meanings as those mentioned above.

The following reaction scheme indicates a method of preparing a compound represented by the general formula (IV) having one or more protective groups (Step A) and removing the protective groups in Step B (therefore, at least one of the groups selected from the group consisting of $R^4$, $R^5$, and $R^6$ has a protective group). When two or more protective groups are present, the deprotection in Step B is performed by a step of removing the protective groups stepwise, or a step of simultaneously removing all the protective groups. However, the method for preparing the compounds of the present invention represented by the general formula (I) is not limited to the following method. Further, the scope of the compounds of the present invention represented by the general formula (I) is not limited to those prepared by the following method.

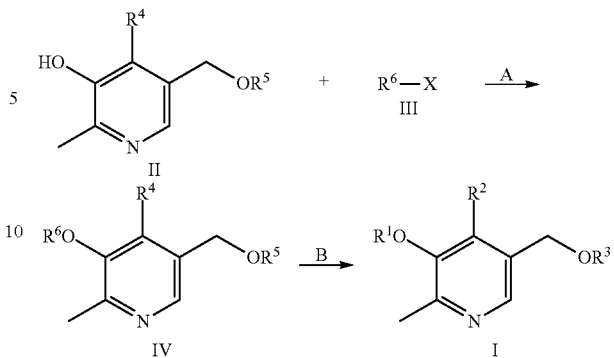

First, a compound represented by the general formula (II) and a compound represented by the general formula (III) are subjected to a glycosylation reaction to prepare a compound represented by the general formula (IV). In this reaction, an activator may be used or may not be used. As the compounds represented by the general formula (II), for example, $\alpha^4,\alpha^5$-di-O-acetylpyridoxine, and $\alpha^4,\alpha^5$-di-O-benzoylpyridoxine can be obtained by the method described by W. Korytnyk et al. (J. Org. Chem., 32, 3791-3796, 1967), for example, $\alpha^4,\alpha^5$-O-isopropylidene pyridoxine can be obtained by the method described by Mizuno et al. (Vitamins, 49, 395-401, 1975), and for example, pyridoxal monoethylacetal can be obtained by the method described by D. Heyl et al. (J. Am. Chem. Soc., 73, 3430-3439, 1951).

In the compounds represented by the general formula (II), as the protective group of the hydroxyl group in $R^4$, for example, acetyl group, benzoyl group, benzyl group, tert-butyldimethylsilyl group, tetrahydropyranyl group, isopropylidene group, isobutylidene group and the like can be used, as the protective group of the formyl group in $R^4$, for example, acetyl group, a cyclic acetal group and the like can be used, and as the protective group of the amino group in $R^4$, for example, acetyl group, benzoyl group, benzyl group, tert-butoxycarbonyloxy group and the like can be used. As $R^5$, hydrogen atom, a protective group of hydroxyl group (for example, acetyl group, benzoyl group, benzyl group, tert-butyldimethylsilyl group, tetrahydropyranyl group, isopropylidene group, isobutylidene group and the like), or a phosphate or a protected phosphate (for example, diethyl phosphate, di-tert-butyl phosphate, dibenzyl phosphate and the like) can be used. In addition, $R^4$ and $R^5$ may combine with each other to represent a protective group forming a ring. Examples of the protective group formed by $R^4$ and $R^5$ combined with each other include isopropylidene group, isobutylidene group, monomethylacetal group, monoethylacetal group and the like.

The compound represented by the general formula (III) is a compound comprising a saccharide compound of which hydroxyl group at the 1-position (2-position for fructose) is substituted with X. It is preferred that a part or all of the other hydroxyl groups are protected, and it is more preferred that all of the other hydroxyl groups are protected. This compound can be easily obtained by those skilled in the art according to the methods described in Jikken-Kagaku-Koza (Lecture of Experimental Chemistry) 26, 4th edition, Organic Synthesis VIII (edited by Chemical Society of Japan, Maruzen, 1992); Theodora W Green ed., "Protective Groups in Organic Syntheses", John Wiley & Sons, Inc., 1999 and the like.

The type of the protective group of hydroxyl group is not particularly limited, and any of those ordinarily usable as a protective group for protecting hydroxyl group may be used.

All of the protective groups may be the same, or a part or all of the protective groups may be different kinds of protective groups. The protective group of hydroxyl group may form a ring with another protective group. As the protective group of hydroxyl group, for example, acetyl group, benzoyl group, benzyl group and the like are preferred.

The type of the leaving group represented by X is not particularly limited so long as the group can leave in a glycosyl bond forming reaction (namely, a substitution reaction of the compound represented by the general formula (II) with phenolic hydroxyl group), and for example, hydroxyl group, an alkanoyloxy group such as acetyloxy group, a halogen atom such as iodine, chlorine, bromine, and fluorine, trichloroacetimidate group, N-methylacetimidate group, thiomethyl group, thiophenyl group and the like can be used. As the saccharide compound, a saccharide compound explained for $R^1$ can be used. The ratio of the compound represented by the general formula (II) and the compound represented by the general formula (III) is not particularly limited, and either may be used in excess. The reaction can be performed with a molar ratio of the compound represented by the general formula (II) and the compound represented by the general formula (III) in the range of, for example, 0.01 to 100, preferably 0.5 to 2.

The amount of the activator used in this reaction is not particularly limited, and a suitable amount can be chosen within a range of from a catalytic amount to large excess amount depending on the type of the activator. For example, the amount can be selected from a range of 0.01 to 100 equivalents based on either of a molar equivalent of the compound represented by the general formula (II) or that of the compound represented by the general formula (III) which molar equivalent is smaller. Examples of the activator include, for example, mercuric bromide ($HgBr_2$), mercury cyanide ($Hg(CN)_2$), silver trifluoromethanesulfonate ($AgOSO_2CF_3$), silver perchlorate ($AgClO_4$), silver carbonate ($Ag_2CO_3$), silver oxide ($Ag_2O$), silver silicate, silver zeolite, silver tetrafluoroborate ($AgBF_4$), silver p-toluenesulfonate (p-$MeC_6H_5SO_3Ag$), tetraethylammonium bromide ($Et_4NBr$), tetrabutylammonium bromide (n-$Bu_4NBr$), p-toluenesulfonic acid (p-TsOH), tin(II) chloride ($SnCl_2$), tin(IV) chloride ($SnCl_4$), trimethylsilyl triflate ($Me_3SiOSO_2CF_3$), boron trifluoride ether complex ($BF_3.OEt_2$), silicon tetrafluoride ($SiF_4$), methyl triflate ($CH_{30}SO_2CF_3$), copper(II) bromide ($CuBr_2$), N-bromosuccinimide (NBS), N-iodosuccinimide (NIS), trifluoromethanesulfonic acid ($CF_3SO_3H$), iodonium dicollidine perchlorate (IDCP), trifluoromethanesulfonic acid anhydride (($CF_3SO_2)_2O$), dimethylmethylthiosulfonium triflate ($CH_3SS+(CH_3)_2.CF_3SO^{3-}$), benzeneselenenyl chloride ($C_6H_5SeCl$), methyl thiobromide ($CH_3SBr$), trityl perchlorate ($TrClO_4$) and the like, and silver carbonate, silver oxide, silver perchlorate, silver trifluoromethanesulfonate and the like are preferably used. Two or more kinds of activators may be used in combination.

The type of the reaction solvent is not particularly limited, so long as the solvent does not inhibit the progress of the reaction and successfully dissolves the starting materials. For example, a reaction solvent can be used in the same amount to an amount of 100 times, preferably 5 to 20 times, based on the starting materials. Specific examples include, for example, methylene chloride ($CH_2Cl_2$), chloroform ($CHCl_3$), dichloroethane ($ClCH_2CH_2Cl$), benzene, toluene, acetonitrile, dimethylformamide (DMF), dimethylacetamide (DMAc), diethyl ether, tetrahydrofuran (THF), nitromethane ($CH_3NO_2$) and the like, and methylene chloride, toluene and the like is preferably used. A mixture of two or more kinds of organic solvents may also be used. A reaction temperature is usually in the range of −100 to 150° C., preferably 0 to 100° C. A reaction time varies depending of starting materials, a solvent, a reaction temperature applied and the like, and for example, about 1 to 72 hours, preferably 2 to 24 hours.

Subsequently, one or more protective groups existing in the compound represented by the general formula (IV) can be removed to prepare the compound represented by the general formula (I). For example, when the protective group is acetyl group, deacetylation can be attained by alkali hydrolysis. The base used for the hydrolysis is not particularly limited so long as the base is used as a base in ordinary reactions. Examples include, for example, sodium hydroxide, potassium hydroxide, sodium carbonate, potassium carbonate, sodium hydrogencarbonate, sodium hydride, lithium hydride, aqueous ammonia and the like, and sodium hydroxide or potassium hydroxide can be preferably used. The type of the reaction solvent is not particularly limited so long as the solvent does not inhibit the progress of the reaction and successfully dissolves the starting material. Examples include, for example, alcohols (methanol, ethanol and the like), DMF, DMAc, diethyl ether, tetrahydrofuran, dioxane, water, acetone, mixtures thereof and the like, and alcohols, water, and mixtures thereof are preferred. A reaction temperature is usually −20 to 150° C., preferably 10 to 30° C. A reaction time varies depending of starting materials, a solvent, a reaction temperature applied and the like, and is usually about 5 minutes to 36 hours, preferably 10 minutes to 16 hours.

For example, when the protective group is benzyl group, debenzylation can be attained by hydrogenation. A catalyst such as palladium/carbon or platinum can be used as a hydrogenation catalyst. Palladium/carbon is preferred. The type of a reaction solvent is not particularly limited so long as an inert organic solvent that does not act as a catalyst poison is chosen. For example, an alcohol (methanol, ethanol and the like), DMF, DMAc, acetic acid, water, or a mixture of these is used, and methanol or acetic acid can be preferably used. A reaction temperature is usually 0 to 50° C., preferably 10 to 30° C. A reaction time varies depending of a starting material, a solvent, a reaction temperature and the like, and is usually about 1 to 24 hours, preferably 1 to 16 hours.

For example, when the protective group is isobutylidene group or monoethylacetal group, deacetalation or removal of isobutylidene can be attained by acidolysis. The acid used for the acidolysis is not particularly limited so long as the acid is used as an acid in ordinary reactions. Examples include hydrochloric acid, aqueous hydrogen bromide, sulfuric acid, acetic acid, p-toluenesulfonic acid and the like, and hydrochloric acid, acetic acid and the like can be preferably used. A reaction solvent is not particularly limited, so long as the solvent does not inhibit the progress of the reaction and successfully dissolves the starting material. Examples include, for example, alcohols (methanol, ethanol and the like), DMF, DMAc, diethyl ether, tetrahydrofuran, dioxane, water, acetone, mixtures thereof and the like, and alcohols, water, and mixtures thereof are preferred. A reaction temperature is usually −20 to 150° C., preferably 10 to 100° C. A reaction time varies depending of a starting material, a solvent, a reaction temperature applied and the like, and is usually about 5 minutes to 36 hours, preferably 10 minutes to 16 hours.

If necessary, the compound of the general formula (IV) wherein $R^4$ is —$CH_2$-amino acid or —$CH_2NH_2$ can be prepared by condensing a compound of the general formula (IV) wherein $R^4$ is —CHO with an amino acid or hydroxylamine, and hydrogenating the resulting compound. It is preferred that the N-terminus amino group of the amino acid is unsubstituted, and the carboxyl group of the C-terminus and functional groups of side chain may be unsubstituted or protected.

This compound can be easily obtained by those skilled in the art according to a method described in, for example, Izumiya. N. et al. Ed., "Fundamentals and Experiments of Peptide Synthesis" (Maruzen Co., Ltd., 1985) and the like.

The condensation may be carried out in the presence of a base. The base to be used is not particularly limited so long as the base is used as a base in ordinary reactions. Examples include, for example, inorganic bases such as sodium hydroxide, potassium hydroxide, calcium hydroxide, barium hydroxide, sodium carbonate, potassium carbonate, calcium carbonate, barium carbonate, sodium hydrogencarbonate, potassium hydrogencarbonate, calcium oxide, barium oxide, and sodium acetate, and organic bases such as ammonia, dimethylamine, triethylamine, trimethylamine, dicyclohexylamine, dimethylaniline, pyridine, N-methylmorpholine, N-ethylpiperidine, lutidine, collidine, and quinoline, and potassium hydroxide, sodium acetate, triethylamine and the like is preferably used. The reaction solvent is not particularly limited, so long as the solvent does not inhibit the progress of the reaction and successfully dissolves the starting materials. Examples include, for example, alcohols (methanol, ethanol and the like), DMF, DMAc, diethyl ether, tetrahydrofuran, dioxane, water, acetone, mixtures thereof and the like, and alcohols, water, and mixtures thereof are preferred. The reaction temperature is usually −20 to 150° C., preferably 20 to 100° C. A reaction time varies depending of starting materials, a solvent, a reaction temperature applied and the like, and is usually about 5 minutes to 72 hours, preferably 10 minutes to 16 hours.

As the hydrogenation catalyst used for the hydrogenation, a catalyst such as palladium/carbon, and platinum can be used, and as the hydrogenation agent, reagents such as $NaBH_4$, $NaBH_3CN$, and $NaBH(OMe)_3$ can be used. Preferred examples include palladium/carbon and $NaBH_4$. A reaction solvent is not particularly limited so long as an inert organic solvent that does not act as a catalyst poison is chosen. For example, alcohols (methanol, ethanol and the like), DMF, DMAc, acetic acid, water, mixtures thereof are used, and methanol, water and mixtures thereof can be preferably used. The reaction temperature is usually 0 to 50° C., preferably 10 to 30° C. A reaction time varies depending of a starting material, a solvent, a reaction temperature applied and the like, and is usually about 1 to 24 hours, preferably 1 to 16 hours.

The phosphoric acid ester compounds of the present invention represented by general formula (I) can be prepared according to, for example, the following reaction scheme. $R^1$, $R^2$, $R^3$, $R^4$, $R^5$, and $R^6$ in the reaction scheme have the same meanings as those defined above. In the following reaction scheme, a method of preparing a compound represented by the general formula (IV) having one or more protective groups (Step C) and removing the protective groups in Step B is mentioned (therefore, at least one among those groups selected from $R^4$, $R^5$, and $R^6$ has a protective group). When two or more protective groups are present, the deprotection in Step B is performed by a step of removing them stepwise, or a step of simultaneously removing all the protective groups. However, the method for producing the compounds of the present invention represented by the general formula (I) is not limited to the following method. Moreover, the scope of the compounds of the present invention represented by the general formula (I) is not limited to those prepared by the following method.

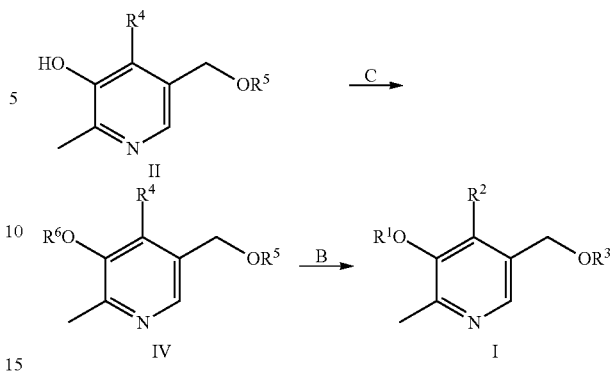

First, in the presence of a base, a compound represented by the general formula (II) and a phosphorylation agent are subjected to a phosphorylation reaction to prepare a compound represented by the general formula (IV). As for the compounds represented by the general formula (II), for example, $\alpha^4,\alpha^5$-di-O-acetylpyridoxine, $\alpha^4,\alpha^5$-di-O-benzoylpyridoxine and the like can be obtained by the method described by W Korytnyk et al. (J. Org. Chem., 32, 3791-3796, 1967), for example, $\alpha^4,\alpha^5$-O-isopropylidene pyridoxine can be obtained by the method described by Mizuno et al. (Vitamin, 49, 395-401, 1975), and for example, pyridoxal monoethylacetal can be obtained by the method described by D. Heyl et al. (J. Am. Chem. Soc., 73, 3430-3439, 1951).

In the compounds represented by the general formula (II), as the protective group of the hydroxyl group in $R^4$, for example, acetyl group, benzoyl group, benzyl group, tert-butyldimethylsilyl group, tetrahydropyranyl group, isopropylidene group, isobutylidene group and the like can be used, as the protective group of the formyl group in $R^4$, for example, acetyl group, a cyclic acetal group and the like can be used, and as the protective group of the amino group in $R^4$, for example, acetyl group, benzoyl group, benzyl group, tert-butoxycarbonyloxy group and the like can be used. As $R^5$, hydrogen atom, a protective group of hydroxyl group (for example, acetyl group, benzoyl group, benzyl group, tert-butyldimethylsilyl group, tetrahydropyranyl group, isopropylidene group, isobutylidene group and the like), or a phosphate or a protected phosphate (for example, diethyl phosphate, di-tert-butyl phosphate, dibenzyl phosphate and the like) can be used. In addition, $R^4$ and $R^5$ may combine with each other to represent a protective group forming a ring. Examples of the protective group formed by $R^4$ and $R^5$ combined with each other include isopropylidene group, isobutylidene group, monomethylacetal group, monoethylacetal group and the like.

As for a ratio of the compound represented by the general formula (II) and the phosphorylation agent, the reaction can be performed with a molar ratio of the phosphorylation agent, for example, in a range of 1 to 20 times, preferably 2 to 10 times, based on the compound represented by the general formula (II).

Examples of the phosphorylation agent include, for example, phosphorous oxychloride, phosphorus oxybromide, phosphorus oxyfluoride, phosphoryl dichloride, phosphoryl chloride, phosphoryl bromide, phosphoric acid, polyphosphoric acid, tetrachloropyrophosphoric acid and the like, and phosphorous oxychloride and the like are preferably used.

The type of a base is not particularly limited. As a mineral base, for example, sodium hydroxide, potassium hydroxide, calcium hydroxide, barium hydroxide, sodium carbonate, potassium carbonate, calcium carbonate, barium carbonate, sodium hydrogencarbonate, potassium hydrogencarbonate, calcium oxide, barium oxide, disodium phosphate, trisodium phosphate, dipotassium phosphate, tripotassium phosphate and the like may be used. Examples of organic base include, for example, ammonia, dimethylamine, triethylamine, trimethylamine, dicyclohexylamine, dimethylaniline, pyridine, N-methylmorpholine, N-ethylpiperidine, lutidine, collidine, quinoline and the like, and pyridine and the like are preferably used.

The type of a reaction solvent is not particularly limited so long as the solvent does not inhibit the progress of the reaction and successfully dissolves the starting materials. Examples include pyridine, DMF, water, acetone, trimethyl phosphate, and mixtures thereof, and pyridine is preferred. For example, a reaction temperature is usually −20 to 100° C., preferably 0 to 50° C. A reaction time varies depending of starting materials, a solvent, a reaction temperature applied and the like, and is, for example, about 5 minutes to 36 hours, preferably 10 minutes to 16 hours.

Subsequently, one or more protective groups existing in the compound represented by the general formula (IV) can be removed to prepare the compound represented by the general formula (I). For example, when the protective group is acetyl group, deacetylation can be attained by alkali hydrolysis. A base used for the hydrolysis is not particularly limited so long as the base used is used as a base in ordinary reactions. Examples include, for example, sodium hydroxide, potassium hydroxide, sodium carbonate, potassium carbonate, sodium hydrogencarbonate, sodium hydride, lithium hydride, aqueous ammonia and the like, and sodium hydroxide, potassium hydroxide, sodium hydrogencarbonate and the like can be preferably used. The type of a reaction solvent is not particularly limited so long as the solvent does not inhibit the progress of the reaction and successfully dissolves the starting material. Examples include, for example, alcohols (methanol, ethanol and the like), DMF, DMAc, diethyl ether, tetrahydrofuran, dioxane, water, acetone, mixtures thereof and the like, and alcohols, water, and mixtures thereof are preferred. A reaction temperature is usually −20 to 150° C., preferably 10 to 30° C. A reaction time varies depending of a starting material, a solvent, a reaction temperature applied and the like, and is usually about 5 minutes to 36 hours, preferably 10 minutes to 16 hours.

For example, when the protective group is benzyl group, debenzylation can be attained by hydrogenation. A catalyst such as palladium/carbon or platinum can be used as a hydrogenation catalyst. Palladium/carbon is preferred. A reaction solvent is not particularly limited so long as an inert organic solvent that does not act as a catalyst poison is chosen. For example, alcohols (methanol, ethanol and the like), DMF, DMAc, acetic acid, water, mixtures thereof are used, and methanol or acetic acid can be preferably used. A reaction temperature is usually 0 to 50° C., preferably 10 to 30° C. A reaction time varies depending of a starting material, a solvent, a reaction temperature applied and the like, and is usually about 1 to 24 hours, preferably 1 to 16 hours.

For example, when the protective group is monoethylacetal group or isobutylidene group, deacetalation or removal of isobutylidene can be attained by acidolysis. An acid used for the acidolysis is not particularly limited so long as the acid is used for ordinary reactions as an acid. Examples include hydrochloric acid, aqueous hydrogen bromide, sulfuric acid, acetic acid, p-toluenesulfonic acid and the like, and hydrochloric acid or acetic acid can be preferably used. A reaction solvent is not particularly limited so long as the solvent does not inhibit the progress of the reaction and successfully dissolves the starting material. Examples include, for example, alcohols (methanol, ethanol and the like), DMF, DMAc, diethyl ether, tetrahydrofuran, dioxane, water, acetone, mixtures thereof and the like, and alcohols, water, and mixtures thereof are preferred. A reaction temperature is usually −20 to 150° C., preferably 10 to 100° C. A reaction time varies depending on a starting material, a solvent, a reaction temperature applied and the like, and is usually 5 minutes to 36 hours, preferably 10 minutes to 16 hours.

The composition of the present invention is a composition containing the vitamin B6 derivative represented by the general formula (V) or a salt thereof. The composition of the present invention is characterized in that the vitamin B6 derivative has superior stability, and also other components in the composition, especially other vitamins, have improved stability, and decrease of contents of the aforementioned vitamin B6 derivative and the other components after storage for a long period of time is reduced.

Purposes of use of the composition of the present invention are not particularly limited. For example, uses as pharmaceutical compositions, food compositions such as processed food, feed compositions such as animal feed, and cosmetic compositions are preferred. The pharmaceutical compositions include pharmaceutical compositions used for prophylactic treatment, diagnosis, and therapeutic treatment of human diseases as well as so called quasi drugs, multivitamin preparations, pharmaceutical compositions used for diseases of mammals other than human and the like. Examples of the pharmaceutical compositions include, for example, powders, granules, grains, tablets (for example, uncoated tablets, film coated tablets, thin layer sugarcoated tablets, sugar-coated tablets, chewable tablets, bilayer tablets and the like), capsules, powder inhalants, solutions, injections of the before use dissolution type provided in a dry powder form and the like. The processed food includes dry food, drinkable food such as nutrition supplement drink, and food additives as well as health food such as supplemental nutrients and food for specified health uses. Examples of the cosmetic compositions include, for example, powders, foundations, lotions, shampoos and the like. However, these compositions are mentioned as mere examples, and the compositions are not limited to these examples.

In the composition of the present invention, a content of the aforementioned vitamin B6 derivative is not particularly limited. The content may be, for example, 0.001% by weight or more, preferably 0.005% by weight or more, based on the total weight of the composition.

The composition of the present invention may be formed in an arbitrary shape by a suitable means such as granulation. Formed products obtained as described above such as those in the form of granules may further be mixed with one or more kinds of ingredients to prepare another composition. The ingredients used for such a purpose may be suitably chosen by those skilled in the art depending on the purpose of use of the composition of the present invention, and types thereof are not particularly limited. For example, for pharmaceutical compositions, ordinarily used pharmaceutical additives (for example, additives for medicaments and the like) can be used, for food compositions such as processed food, food additives can be used, and for cosmetic compositions, additives for cosmetics can be used.

Examples of the ingredients other than the vitamin B6 derivative in the composition of the present invention include, for example, physiologically active substances such as amino acids, lipids, saccharides, hormones, enzymes, and nucleic acids, breast meat of chicken, wheat flour, rice bran and the like. Examples of binders include, for example, hydroxypropylcellulose, hydroxymethylcellulose, hydroxymethylpropylcellulose, polyvinylpyrrolidone, polyvinyl alcohol, dextrin, pullulan, pregelatinized starch, gelatinized starch, gum arabic, gelatin, cellulose acetate phthalate, hydroxypropylmethylcellulose phthalate, ethylcellulose, L-arabinose, D-xylose, D-2-deoxyribose, D-ribose, D- and L-galactose, D-glucose, D-mannose, D-fructose, L-sorbose, L-fucose, L-rhamnose, D-glucosamine, D-sorbitol, D-mannitol, galactitol, erythritol, cellobiose, gentibiose, isomaltose, kojibiose, lactose, lactitol, laminaribiose, maltose, melibiose, nigerose, sophorose, sucrose, paratinose, trehalose, palatinite, dextrin, stearic acid and derivatives thereof, sucrose fatty acid ester, maize starch, Aspartame, stevia, acesulfame, saccharin, aminoalkyl methacrylate copolymer, methacrylic acid copolymer, carboxyvinyl polymer, polyvinyl acetal diethylamine acetate, lactose, xylitol, maltitol, powder reducing sugar starch syrup, arabitol, ribitol, glucitol, corn flour, wheat flour, rice bran, cottonseed meal, sodium arginate, carragheenan, casein, gluten, curdlan, guar gum and the like.

Further, the ingredient other than the vitamin B6 derivative in the composition of the present invention may be a mineral salt, and the composition may contain, for example, sodium chloride, manganese carbonate, zinc sulfate, iron sulfate, hemoferrum, ferritin, ferric phosphate, ferrous succinate, ferrous fumarate, iron lactate, ferric pyrophosphate, ferrous pyrophosphate, iron sesquioxide, ferric citrate, sodium ferrous citrate, ferric ammonium citrate, ferrous gluconate, ferric chloride, zinc acetate, zinc gluconate, zinc oxide, zinc chloride, selenium sulfide, cupric gluconate, copper sulfate, copper chloride, manganese sulfate, manganese glycerophosphate, manganese chloride, manganese hypophosphite, manganese gluconate, magnesium silicate, magnesium oxide, magnesium stearate, magnesium chloride, magnesium carbonate, magnesium sulfate, magnesium gluconate, magnesium salicylate, magnesium hydroxide, magnesium acetate, magnesium(II) phosphate, magnesium(III) phosphate, calcium magnesium carbonate, bovine bone meal, fishbone powder, scallop shell flour, oyster shell flour, ground shell, egg shell powder, whey calcium, calcium gluconate, calcium carbonate, dibasic calcium phosphate, potassium sulfate, potassium iodide and the like. Further, examples of aromatics include, for example, peppermint oil, eucalyptus oil, cinnamon oil, fennel oil, clove oil, orange oil, lemon oil, rose oil, fruit flavors, banana flavor, strawberry flavor, mint flavor, peppermint flavor, dl-menthol, l-menthol and the like. Examples of corrigents include citric acid, malic acid, tartaric acid, ascorbic acid, Aspartame, stevia, saccharin, dipotassium glycyrrhizin, thaumatin, and acesulfame. However, these ingredients are mentioned as mere examples, and the aforementioned ingredients are not limited to these examples.

The compounds represented by the general formula (V) and salts thereof are useful as a stable vitamin B6 derivative, especially a vitamin B6 derivative which is stable against light, in the fields of pharmaceuticals, foodstuffs, feeds, cosmetics and the like. For example, as medicaments, they can be use for prophylactic and/or therapeutic treatment of vitamin B6 deficiency, or prophylactic and/or therapeutic treatment of diseases such as glossitis, gastritis, seborrheic dermatoses of circumferences of eyes, noses and mouth, and infantile convulsion. They can also be administered to patients when the demand of vitamin B6 increases, and intake from meals is insufficient, for example, to patients with wasting diseases, pregnant women, lactating women and the like, as well as at the time of using oral contraceptive, thyroid hyperfunction, radiation irradiation, chronic alcoholism, and administration of antibiotics and the like, as a supplemental medicament. Furthermore, the substance is useful for therapeutic treatment of vitamin B6 dependency (dependent anemia, dependent convulsions and the like), and therapeutic treatment of diseases in which involvement of lack or of vitamin B6 or vitamin B6 metabolic disorder are suspected (for example, angular stomatitis, chilitis, glossitis, acute and chronic eczema, contact dermatitis and the like).

As foodstuffs, the substance can be used, for example, as a component of soft drinks, for enrichment of health-oriented foodstuffs, as a component of supplemental nutrients (supplements) and the like, and can be used in various feeds for enrichment of vitamin B6. For cosmetics, they can be added to, for example, hair cosmetics, skin cosmetics, cosmetics for razors and the like However, purposes of use of the compounds represented by the general formula (V) and salts thereof are not limited to these specific uses.

The cosmetic composition of the present invention, for example, a composition for cosmetics comprising (A) a compound represented by the general formula (V), and (B) one or more kinds of substances selected from the group consisting of a whitening agent, an antioxidant, an anti-inflammatory agent, a blood circulation accelerator, a cell activation agent, and an ultraviolet absorber, exhibits superior effects as a whitening agent, an anti-aging agent and an agent for suppressing wrinkle formation resulting from ultraviolet exposure. A content of the vitamin B6 derivative in the composition is not particularly limited, and the content is preferably 0.00001 to 2.0% by weight, more preferably 0.001 to 1.0% by weight, based on the total weight of the composition. If the content is chosen within the above range, the vitamin B6 derivative can be stably blended, and superior whitening effect, anti-aging effect, and effect of suppressing wrinkle formation resulting from ultraviolet exposure can be obtained.

In the manufacture of the whitening agent, anti-aging agent, and agent for suppressing wrinkle formation resulting from ultraviolet exposure according to the present invention, ingredients ordinarily used for preparations such as those of cosmetics, quasi drugs, and those for external application may be added within an extent that the advantageous effects of the present invention are not inhibited, if necessary, and examples of such ingredients include, for example, water (purified water, hot spring water, deep sea water and the like), oils, surface active agents, metallic soaps, gelatinizers, fine particles, alcohols, water-soluble polymers, film-forming ingredients, resins, clathrate compounds, antimicrobial agents, perfumes, deodorizers, salts, pH adjustors, refrigerants, extracts of plant, animal and microorganism, active oxygen scavengers, blood circulation accelerators, astringents, antiseborrheic agents, moisturizers, chelating agents, keratolytic agents, enzymes, hormones, other vitamins and the like.

EXAMPLES

The present invention will be explained more specifically with reference to the following examples. However, the scope of the present invention is not limited by the following examples.

Example 1

Preparation of pyridoxine 3-β-D-glucoside a) 3-(2,3,4,6-Tetra-O-acetyl-β-D-glucopyranosyl)-$\alpha^4,\alpha^5$-di-O-acetylpyridoxine $\alpha^4,\alpha^5$-Di-O-acetylpyridoxine hydrochloride (4.90 g, 17.2 mmol) was added with CHCl$_3$ (150 ml) and saturated aqueous NaHCO$_3$ (100 ml), and the mixture was stirred at room temperature for 1 hour. Then, the organic layer was washed with saturated brine, and dried over anhydrous MgSO$_4$, and the solvent was evaporated under reduced pressure. The resulting white solid (4.0 g) and 2,3,4,6-tetra-O-acetyl-α-D-glucopyranosyl bromide (9.74 g, 23.7 mmol) were dissolved in CH$_2$Cl$_2$ (70 ml), and the solution was added with silver carbonate (4.36 g, 15.8 mmol) under light shielding and refluxed under a nitrogen atmosphere, and then stirred overnight. The reaction mixture was concentrated under reduced pressure, and then the residue was purified by column chromatography (silica gel, 600 g, eluted with a mixed solvent of n-hexane:ethyl acetate=1:2) to obtain the title compound (7.17 g, yield: 78%) as white solid.

Melting point: 89-93° C.
Specific rotation [α]$_D$=−20° (c=0.2, CHCl$_3$)
$^1$H-NMR (CDCl$_3$) δ ppm: 2.03 (3H, s), 2.04 (3H, s), 2.07 (3H, s), 2.08 (3H, s), 2.09 (3H, s), 2.14 (3H, s), 2.55 (3H, s), 3.5-3.6 (1H, m), 4.0-4.2 (2H, m), 4.83 (1H, d), 5.1-5.4 (7H, m), 8.38 (1H, s)

b) Pyridoxine 3-β-D-glucoside

The compound of Example 1, a) (7.10 g, 12.2 mmol) was dissolved in methanol (40 ml) and water (20 ml), and added with sodium hydroxide (3.38 g, 51.8 mmol) with stirring under ice cooling. The sodium hydroxide was dissolved in the solution, and then the solution was stirred at room temperature for 1 hour. The reaction mixture was neutralized with 1 N hydrochloric acid, and concentrated under reduced pressure, and then the residue was purified by column chromatography (SP850, 100 ml, eluted with water to 20% aqueous methanol). The resulting solid was dissolved in water (200 ml), and added with activated carbon (50% wet, 150 mg), and the mixture was stirred at 60° C. for 30 minutes. The activated carbon was separated by filtration, and then water was evaporated under reduced pressure. The residue was recrystallized from ethanol/water (10:1, 88 ml) to obtain the title compound (3.14 g, yield: 78%) as white crystals. This compound was not hydrolyzed with α-glucosidase (Roche, derived from *Saccharomyces cerevisiae*), and completely hydrolyzed with β-glucosidase (Oriental Yeast, derived from almond) to release pyridoxine. Therefore, the anomer type of this compound was confirmed to be β type.

Melting point: 211-212° C.
Specific rotation [α]$_D$=−6.0° (c=1.0, H$_2$O)
$^1$H-NMR (DMSO-d$_6$) δ ppm: 2.49 (3H, s), 3.0-3.7 (6H, m), 4.3-5.2 (10H, m), 5.59 (1H, d, J=4.8 Hz), 8.25 (1H, s)

Example 2

Preparation of pyridoxal 3-β-D-glucoside a) 3-(2,3,4,6-Tetra-O-acetyl-β-D-glucopyranosyl)-pyridoxal monoethylacetal Pyridoxal monoethylacetal hydrochloride (11.0 g, 47.5 mmol) was suspended in CH$_2$Cl$_2$ (100 ml) under a nitrogen atmosphere, and added with triethylamine (6.63 ml, 47.5 mmol) under ice cooling, and the mixture was warmed to room temperature, and then added with 2,3,4,6-tetra-O-acetyl-α-D-glucopyranosyl bromide (23.4 g, 57.0 mmol). After the reaction vessel was light-shielded, the reaction mixture was added with silver carbonate (13.1 g, 47.5 mmol), and stirred at room temperature for 18 hours, and then stirring was continued at 35° C. for 24 hours. The reaction mixture was filtered, and concentrated under reduced pressure, and then the residue was purified by column chromatography (silica gel, 600 g, eluted with a mixed solvent of n-hexane:ethyl acetate=1:2) to obtain the title compound (20.8 g, 84%).

$^1$H-NMR (CDCl$_3$) δ ppm: 1.2-1.4 (3H, m), 2.0-2.1 (12H, m), 2.45 (1.7H, s), 2.54 (1.3H, s), 3.5-4.3 (5H, m), 4.9-5.6 (6H, m), 6.24 (0.5H, d, J=1.8 Hz), 6.42 (0.5H, d, J=1.7 Hz), 8.16 (0.5H, s), 8.30 (0.5H, s)

b) 3-(2,3,4,6-Tetra-O-acetyl-β-D-glucopyranosyl)-pyridoxal

The compound of Example 2, a) (20.0 g, 38.1 mmol) was added with water (200 ml) and 1 N hydrochloric acid (38 ml), and the mixture was stirred for 30 minutes under reflux. The reaction mixture was cooled to room temperature, then added with saturated sodium hydrogencarbonate (200 ml), and extracted with ethyl acetate (300 ml). The organic layer was dried over anhydrous MgSO$_4$, and concentrated under reduced pressure, and then the residue was purified by column chromatography (silica gel, 600 g, eluted with a mixed solvent of CHCl$_3$:MeOH (methanol)=50:1) to obtain the title compound (10.8 g, 57.0%).

$^1$H-NMR (CDCl$_3$) δ ppm: 2.0-2.1 (12H, m), 2.45 (1.8H, s), 2.54 (1.2H, s), 3.6-4.3 (4H, m), 4.9-5.5 (6H, m), 6.6-6.7 (1H, m), 8.19 (0.6H, s), 8.29 (0.4H, s)

c) Pyridoxal 3-β-D-glucoside

The compound of Example 2, b) (2.0 g, 4.02 mmol) was dissolved in MeOH (25 ml) and water (3 ml), and added with potassium hydroxide (262 mg, 4.02 mmol) dissolved in water (2 ml) with stirring under ice cooling, and the mixture was stirred at room temperature for 1 hour. After disappearance of the starting material was confirmed by TLC, the reaction mixture was neutralized with 1 N hydrochloric acid, and concentrated under reduced pressure, and then the residue was purified by column chromatography (SP850, 100 ml, eluted with water to 30% aqueous MeOH).

The resulting solid was dissolved in water (200 ml), and added with activated carbon (50% wet, 150 mg), and the mixture was stirred at 60° C. for 30 minutes. The activated carbon was separated by filtration, and then the filtrate was lyophilized to obtain the title compound (1.16 g, 88%) as white amorphous powder.

Melting point: 130 to 140° C.
Specific rotation [α]$_D$=−38.4° (c=1.0, H$_2$O)
$^1$H-NMR (DMSO-d$_6$) δ ppm: 2.42 (3H, s), 3.0-3.5 (5H, m), 3.6-3.8 (1H, m), 4.6-5.5 (7H, m), 6.5-6.6 (1H, m), 6.84 (0.4H, d, J=6.6 Hz), 6.98 (0.6H, d, J=7.0 Hz), 8.05 (0.6H, s), 8.20 (0.4H, s).

Example 3

Preparation of pyridoxamine 3-β-D-glucoside a) 3-(2,3,4,6-Tetra-O-acetyl-β-D-glucopyranosyl)-pyridoxal oxime The compound of Example 2, b) (6.0 g, 12.1 mmol) was suspended in water (200 ml), and added with sodium acetate (1.29 g, 15.7 mmol) and hydroxylammonium chloride (1.26 g, 18.2 mmol), and the mixture was stirred for 30 minutes under reflux. The reaction mixture was cooled to room temperature, and then extracted with ethyl acetate (300 ml). The organic layer was dried over anhydrous MgSO$_4$, and then the solvent was evaporated under reduced pressure. The residue was added with diethyl ether, and the deposited solid was collected by filtration, washed with diethyl ether, and then dried under reduced pressure to obtain the title compound (5.49 g, 89%).

$^1$H-NMR (CDCl$_3$) δ ppm: 2.03 (3H, s), 2.03 (3H, s), 2.05 (3H, s), 2.19 (3H, s), 2.56 (3H, s), 3.5-3.7 (1H, m), 4.0-4.2 (2H, m), 4.61 (2H, brs), 4.80 (1H, d, J=7.9 Hz), 5.0 (1H, brs), 5.1-5.5 (3H, m), 8.40 (1H, s), 8.57 (1H, s), 10.9 (1H, brs)

b) 3-(2,3,4,6-Tetra-O-acetyl-β-D-glucopyranosyl)-pyridoxamine

The compound of Example 3, a) (2.28 g, 4.41 mmol) was dissolved in acetic acid (60 ml), and subjected to catalytic hydrogenation at room temperature for 1 hour in the presence of 5% Pd—C (AD, 50% wet, 1.2 g). The catalyst was separated by filtration, and then the acetic acid was evaporated under reduced pressure. The residue was purified by column chromatography (silica gel, 50 g, eluted with CHCl$_3$:MeOH:AcOH (acetic acid)=10:1:0.01) to obtain the title compound (1.97 g, 90%).

$^1$H-NMR (CDCl$_3$) δ ppm: 2.01 (3H, s), 2.05 (6H, s), 2.16 (3H, s), 2.53 (3H, s), 3.5-5.4 (14H, m), 8.32 (1H, s)

c) Pyridoxamine 3-β-D-glucoside

The compound of Example 3, b) (1.90 g, 3.81 mmol) was dissolved in methanol (25 ml) and water (3 ml), and added with potassium hydroxide (498 mg, 7.62 mmol) dissolved in water (4 ml) with stirring under ice cooling, and the mixture was stirred at room temperature for 1 hour. After disappearance of the starting material was confirmed, the reaction mixture was neutralized with 6 N hydrochloric acid, and concentrated under reduced pressure, and the residue was dissolved in water (50 ml), adjusted to pH 10 with 1 N sodium hydroxide, and purified by column chromatography (SP850, 100 ml, eluted with water to 30% aqueous MeOH). The resulting solid was dissolved in water (200 ml), and added with activated carbon (50% wet, 250 mg), and the mixture was stirred at 60° C. for 30 minutes. The activated carbon was separated by filtration, and then the filtrate was lyophilized to obtain the title compound (189 mg, 18%) as white amorphous powder.

Melting point: 205 to 212° C.
Specific rotation [α]$_D$=−6.1° (c=1.0, H$_2$O)
$^1$H-NMR (DMSO-d$_6$) δ ppm: 2.49 (3H, s), 3.0-3.5 (10H, m), 3.6-3.8 (2H, m), 4.02 (1H, d, J=12.0 Hz), 4.3-4.7 (3H, m), 5.0-5.1 (2H, m), 8.15 (1H, s)

Example 4

Preparation of pyridoxine 3-β-D-galactoside a) 3-(2,3,4,6-Tetra-O-acetyl-β-D-galactopyranosyl)-α$^4$,α$^5$-di-O-acetyl-pyridoxine α$^4$,α$^5$-Di-O-acetylpyridoxine hydrochloride (7.82 g, 27.0 mmol) was added with CHCl$_3$ (300 ml) and saturated aqueous NaHCO$_3$ (200 ml), and the mixture was stirred at room temperature for 1 hour. Then, the organic layer was washed with saturated brine, and dried over anhydrous MgSO$_4$, and then the solvent was evaporated under reduced pressure. The resulting white solid (11.4 g, 27.0 mmol) and 2,3,4,6-tetra-O-acetyl-β-D-galactopyranosyl bromide were dissolved in CH$_2$Cl$_2$ (60 ml), and added with silver carbonate (6.70 g, 24.3 mmol), and the mixture was stirred at room temperature for 15 hours and under reflux for 7 hours under a nitrogen atmosphere and light shielding. Insoluble solids were separated by filtration, and then the solvent was evaporated under reduced pressure. The residue was purified by column chromatography (silica gel, 700 g, eluted with a mixed solvent of hexane:ethyl acetate=1:3) to obtain the title compound (8.23 g, 58%) as white solid.

$^1$H-NMR (CDCl$_3$) δ ppm: 1.97 (3H, s), 2.02 (3H, s), 2.09 (3H, s), 2.10 (3H, s), 2.15 (3H, s), 2.22 (3H, s), 2.56 (3H, s), 3.7-3.9 (1H, m), 4.0-4.2 (2H, m), 4.79 (1H, d, J=8.1 Hz), 5.0-5.6 (7H, m), 8.39 (1H, s)

b) Pyridoxine 3-β-D-galactoside

The compound of Example 4, a) (8.20 g, 14.1 mmol) was dissolved in methanol (80 ml), and then added with potassium hydroxide (5.99 g, 91.8 mmol) dissolved in water (20 ml) under ice cooling, and the mixture was stirred at room temperature for 30 minutes. After disappearance of the starting material was confirmed, the reaction mixture was neutralized with 6 N hydrochloric acid, and concentrated under reduced pressure, and then the residue was purified by column chromatography (SP850, 100 ml, eluted with water to 15% aqueous MeOH). The resulting solid was dissolved in water (400 ml), and added with activated carbon (50% wet, 500 mg), and the mixture was stirred at 60° C. for 30 minutes. The activated carbon was separated by filtration, and then water was evaporated under reduced pressure. The residue was recrystallized from ethanol/water (2:1, 150 ml) to obtain the title compound (3.67 g, 79%) as colorless needle-like crystals.

Melting point: 215° C. or higher
Specific rotation [α]$_D$=+4.5°=1.0, H$_2$O)
$^1$H-NMR (DMSO-d$_6$) δ ppm: 2.49 (3H, s), 3.2-3.7 (6H, m), 4.4-4.9 (9H, m), 5.20 (1H, t), 5.45 (1H, d, J=5.0 Hz), 8.25 (1H, s)

Example 5

Preparation of N-(4-pyridoxylmethylene)-L-serine 3-β-D-glucoside

L-Serine (1.06 g, 10.1 mmol) was suspended in MeOH (50 ml), and the suspension was stirred, and added with 50% potassium hydroxide (1.12 ml, 10 mmol) so that the potassium hydroxide was dissolved in the suspension. The reaction mixture was added with the compound of Example 2, b) (5.0 g, 10.1 mmol), stirred at room temperature for 30 minutes, and then subjected to catalytic hydrogenation at room temperature for 16 hours in the presence of 5% Pd—C (AD, 50% wet, 5.0 g). The deposited crystals were added with AcOH (1.2 ml) and water (10 ml) so that the crystals were dissolved. The catalyst was separated by filtration, and then the solvent was evaporated under reduced pressure. The residue was purified by reverse phase column chromatography (Chromatorex ODS-1020T, 250 g, eluted with water). The resulting solid was dissolved in water (100 ml), and added with activated carbon (50% wet, 500 mg), and the mixture was stirred at 60° C. for 30 minutes. The activated carbon was separated by filtration, and then the filtrate was concentrated to dryness. The resulting white solid was recrystallized from 90% ethanol (100 ml) to obtain the title compound (2.38 g, 56.9%) as white crystals.

Melting point: 165 to 175° C.
Specific rotation [α]$_D$=+8.8° (c=1.0, H$_2$O)
$^1$H-NMR (DMSO-d$_6$) δ ppm: 2.49 (3H, s), 3.0-3.7 (14H, m), 4.0-4.2 (2H, m), 4.56 (2H, s), 4.68 (1H, d, J=7.5 Hz), 5.1 (3H, brs), 8.21 (1H, s).

Example 6

Preparation of pyridoxine 3,4'-cyclic sodium phosphate a) 3-Phosphoryl-$\alpha^4,\alpha^5$-di-O-acetylpyridoxine $\alpha^4,\alpha^5$-Di-O-acetylpyridoxine hydrochloride (33.3 g, 131 mmol) was dissolved in pyridine (350 ml), and added dropwise with a solution of phosphorous oxychloride (61.3 ml, 657 mmol) in pyridine (150 ml) over 1.5 hours under water cooling. The mixture was stirred for 1 hour, then warmed to 40° C., and stirred for 15 hours. The reaction mixture was concentrated under reduced pressure, and the residue was added with acetonitrile (100 ml) and water (400 ml) under ice cooling. The reaction mixture was stirred for 1.5 hours, added with 28% aqueous ammonia, adjusted to pH 7.0, and then concentrated under reduced pressure. The residue was purified by column chromatography (silica gel, 250 g, eluted with a mixed solvent of $CHCl_3$:MeOH=10:1→5:1) to obtain the title compound (25.6 g, 59%).

$^1$H-NMR (DMSO-$d_6$) δ ppm: 1.98 (3H, s), 2.05 (3H, s), 2.49 (3H, s), 5.14 (2H, s), 5.31 (2H, s), 6.9-7.3 (1H, m), 8.22 (1H, s)

b) Pyridoxine 3,4'-cyclic phosphoric acid

The compound of Example 6, a) (25.6 g, 76.8 mmol) was dissolved in methanol (150 ml) and water (100 ml), and then added with sodium hydroxide (6.34 g, 154 mmol) dissolved in water (100 ml) under ice cooling, and the mixture was stirred at room temperature for 1 hour. After disappearance of the starting material was confirmed, the reaction mixture was neutralized with 2 N hydrochloric acid, and concentrated under reduced pressure, and then the residue was purified by column chromatography (silica gel, 250 g, eluted with a mixed solvent of $CHCl_3$:MeOH=5:1→4:1→2:1). The resulting product was dissolved in water (254 ml), and the solution was adjusted to pH 3.2 by addition of ion exchange resin (DOWEX 50 WX8, 15 g), and then desalted by column chromatography (SP207, 800 ml, eluted with water). The target fractions were concentrated under reduced pressure, and then the reside was dissolved in water (300 ml), and added with activated carbon (50% wet, 1.5 g). The mixture was stirred at 50° C. for 30 minutes, subjected to membrane filtration, and then lyophilized to obtain the title compound (10.4 g, 58%) as white amorphous powder.

$^1$H-NMR (DMSO-$d_6$) δ ppm: 2.44 (3H, s), 3.89 (2H, brs), 4.50 (2H, s), 5.22 (2H, d, J=11.7 Hz), 8.12 (1H, s)

c) Pyridoxine 3,4'-cyclic sodium phosphate

The compound of Example 6, b) (10.4 g, 45 mmol) was dissolved in water (80 ml), and the solution was adjusted to pH 10 by addition of 1 N sodium hydroxide, and desalted by column chromatography (SP207, 800 ml, eluted with water). The target fractions were collected, added with activated carbon (50% wet, 1 g), stirred at 50° C. for 30 minutes, subjected to membrane filtration, and then evaporated to dryness under reduced pressure. The residue was added with ethanol (40 ml) and diethyl ether (300 ml), and the deposited crystals were collected by filtration, and dried under reduced pressure to obtain the title compound (9.63 g, 85%) as white crystals.

Melting point: 190 to 200° C.

$^1$H-NMR (DMSO-$d_6$) δ ppm: 2.28 (3H, s), 4.37 (2H, d, J=3.5 Hz), 5.07 (2H, d, J=5.9 Hz), 5.22 (1H, brs), 7.89 (1H, s)

Example 7

Pyridoxine 3,4'-cyclic magnesium phosphate

The compound of Example 6, b) (20.0 g, 86.5 mmol) was dissolved in water (500 ml), and the solution was adjusted to pH 7.5 by addition of magnesium oxide (1.6 g), and desalted by column chromatography (SP207, 1,000 ml, eluted with water). The target fractions were collected, added with activated carbon (50% wet, 1 g), stirred at 50° C. for 30 minutes, subjected to membrane filtration, and then evaporated under reduced pressure to dryness. The residue was added with acetone (40 ml), and the deposited crystals were collected by filtration, and dried under reduced pressure to obtain the title compound (12.2 g, 58%) as white crystals.

Melting point: 230° C. or higher $^1$H-NMR ($D_2O$) δ ppm: 2.42 (3H, s), 4.60 (2H, s), 4.83 (1H, s), 5.38 (2H, d, J=12.3 Hz), 8.02 (1H, s)

Example 8

Preparation of pyridoxine 3-disodium phosphate

The compound of Example 6, a) (1.0 g, 3.0 mmol) was dissolved in methanol (10 ml), and then added with sodium hydrogencarbonate (0.50 g, 6.0 mmol) dissolved in water (10 ml) under ice cooling, and the mixture was stirred at room temperature for 24 hours. The reaction mixture was neutralized with 2 N hydrochloric acid, and concentrated under reduced pressure, and then the residue was purified by column chromatography (silica gel, 30 g, eluted with a mixed solvent of $CHCl_3$:MeOH=4:1→2:1): The target fractions were concentrated under reduced pressure, and then the residue was dissolved in water (10 ml), and purified by reverse phase column chromatography (Chromatorex ODS-1020T, 30 g, eluted with water). The target fractions were concentrated to 30 ml under reduced pressure, then added with activated carbon (50% wet, 1 g), stirred at 50° C. for 30 minutes, subjected to membrane filtration, and then lyophilized to obtain the title compound (0.299 g, 34%) as white amorphous powder.

Melting point: 137 to 140° C.

$^1$H-NMR (DMSO-$d_6$) δ ppm: 2.39 (3H, s), 4.49 (2H, d, J=6.6 Hz), 4.61 (2H, d, J=4.2 Hz), 5.14 (1H, t), 5.93 (1H, t), 8.17 (1H, s)

Example 9

Preparation of pyridoxine 3-β-D-glucoside hydrochloride

The compound of Example 1, b) (2.0 g, 6.0 mmol) was dissolved in water (150 ml), and added with 1 N hydrochloric acid (6.0 ml), and the mixture was stirred at room temperature for 1 hour. Then, water was evaporated under reduced pressure. The residue was dissolved in ethanol (130 ml) and water (10 ml) under reflux, and cooled in a refrigerator (5° C.) for 5 days. The deposited crystals were collected by filtration, and dried under reduced pressure to obtain the title compound (1.84 g, yield: 83%) as white crystals.

Specific rotation $[\alpha]_D$=+1.7° (c=1.0, $H_2O$), Melting point: 166 to 170° C.

$^1$H-NMR (DMSO-$d_6$) δ ppm: 2.73 (3H, s), 3.3-3.4 (1H, m), 3.5-3.7 (2H, m), 3.7-3.9 (3H, m), 4.7-5.0 (12H, m), 8.47 (1H, s)

Example 10

Preparation of pyridoxine 3-α-D-glucoside a) 3-(3,4,6-Tri-O-acetyl-α-D-glucopyranosyl)-α$^4$,α$^5$-di-O-acetylpyridoxine α$^4$,α$^5$-Di-O-acetylpyridoxine hydrochloride (0.67 g, 2.34 mmol) was added with CHCl$_3$ (10 ml) and saturated aqueous NaHCO$_3$ (10 ml), and the mixture was stirred at room temperature for 1 hour. Then, the organic layer was washed with saturated brine, and dried over anhydrous MgSO$_4$, and then the solvent was evaporated under reduced pressure. The resulting white solid (0.59 g) and 3,4,6-tri-O-acetyl-β-D-glucopyranosyl chloride (0.50 g, 1.54 mmol) were dissolved in toluene (10 ml), and the solution was added with Molecular sieves 4 A (0.50 g), and stirred at 100° C. for 2 hours under a nitrogen atmosphere. The reaction mixture was concentrated under reduced pressure, and then the residue was purified by column chromatography (silica gel, 50 g, eluted with a mixed solvent of n-hexane:ethyl acetate=1:2) to obtain a mixture of the title compound and 3-(3,4,6-tri-O-acetyl-8-D-glucopyranosyl)-α$^4$,α$^5$-di-O-acetylpyridoxine (0.38 g, yield: 46%, α:β=0.3:0.7) as pale yellow oil.

$^1$H-NMR (CDCl$_3$) δ ppm: 2.0-2.2 (15H, m), 2.59 (2.3H, s), 2.67 (0.7H, s), 3.4-4.8 (6H, m), 5.0-5.6 (6H, m), 8.35 (0.2H, s), 8.38 (0.8H, s)

b) Pyridoxine 3-α-D-glucoside

The compound of Example 10, a) (0.37 g, 0.69 mmol) was dissolved in methanol (4 ml) and water (2 ml), and added with potassium hydroxide (0.34 g, 5.15 mmol) with stirring under ice cooling so that the potassium hydroxide was dissolved in the solution. Then, the solution was stirred at room temperature for 1 hour. The reaction mixture was neutralized with 1 N hydrochloric acid, and concentrated under reduced pressure, and then the residue was dissolved in water (14 ml), added with 1 M sodium acetate buffer (1.6 ml) and β-glucosidase (Oriental Yeast, derived from almond, 4 mg, 147 U), and incubated at 37° C. for 14 hours. The reaction mixture was concentrated under reduced pressure, and then the residue was purified by column chromatography (Chromatorex ODS-1020T, 10 g, eluted with water). The resulting solid was dissolved in water (10 ml), and added with activated carbon (50% wet, 10 mg), and the mixture was stirred at 60° C. for 30 minutes. The activated carbon was separated by filtration, and then water was evaporated under reduced pressure to obtain the title compound (54 mg, yield: 24%) as white crystalline powder. This compound was not hydrolyzed with α-glucosidase (Oriental Yeast, derived from almond), and completely hydrolyzed with α-glucosidase (Roche, derived from *Saccharomyces cerevisiae*) to release pyridoxine. Therefore, the anomer type of this compound was confirmed to be α type.

Specific rotation [α]$_D$=+141.8° (c=1.0, H$_2$O), Melting point: 201 to 202° C.

$^1$H-NMR (DMSO-d$_6$) δ ppm: 2.49 (3H, s), 3.1-3.5 (3H, m), 3.5-3.7 (2H, m), 3.8-3.9 (1H, m), 4.5-4.8 (5H, m), 4.9-5.1 (3H, m), 5.1-5.3 (2H, m), 5.45 (1H, d, J=5.3 Hz), 8.16 (1H, s)

Test Example 1

Light Stability of Pyridoxine 3-β-D-glucoside

A 0.5% (w/v) aqueous solution of pyridoxine 3-β-D-glucoside (pH 6.7) in a volume of 0.3 ml was enclosed in a 1-ml volume glass ampoule, and irradiated with a D65 fluorescent lamp (Toshiba) for 14 days. The irradiation was performed at room temperature with an illumination of 13,000 Lx. Samples before the irradiation and after 1 day, 7 days and 14 days of the irradiation were analyzed by HPLC to measure a pyridoxine 3-β-D-glucoside content. A solution of pyridoxine hydrochloride of the same concentration (adjusted to pH 6.7) was treated in the same manner, and the results were compared. The HPLC measurement conditions were as follows.

Column: Inertsil ODS-3 (5 μm, (5 μm, φ4.6×150 mm, GL Science Inc.)

Eluent acetonitrile:0.1% (v/v) trifluoroacetic acid, 5 mM sodium 1-hexanesulfonate=1:9

Flow rate: 0.5 ml/min

Detection: UV 280 nm

Column temperature: 40° C.

Figure 1:
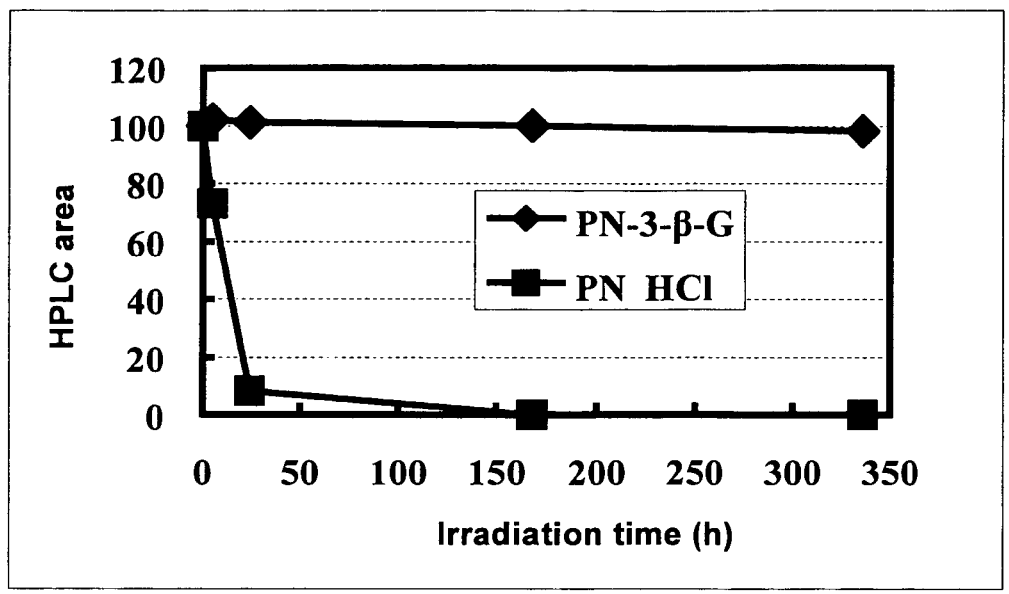
FIG. 1 shows light stability of the compound of the present invention. PN-3-β-G represents pyridoxine 3-β-D-glucoside, and PN.HCl represents pyridoxine hydrochloride.

The results are shown in FIG. 1. Pyridoxine hydrochloride was almost completely decomposed in one day, whilst decomposition of pyridoxine 3-β-D-glucoside was not observed even after the irradiation with the lamp for 14 days, and thus it was found that the light stability thereof was remarkably improved. Moreover, the aqueous solution of pyridoxine hydrochloride colored in pale yellow after the light irradiation, whilst no coloring was observed for the aqueous solution of pyridoxine 3-β-D-glucoside.

Test Example 2

Thermal Stability of Pyridoxine 3-β-D-glucoside

A 0.5% (w/v) aqueous solution of pyridoxine 3-β-D-glucoside (pH 6.7) in a volume of 0.3 ml was sealed in a 1-ml volume glass ampoule, and kept at 50° C. under light shielding. The sample was warmed for 90 days, and analyzed during the warming by HPLC (analysis conditions were the same as those applied in Test Example 1) to measure a pyridoxine 3-β-D-glucoside content. A solution of pyridoxine hydrochloride of the same concentration (adjusted to pH 6.7) was treated in the same manner, and the results were compared.

Figure 2:
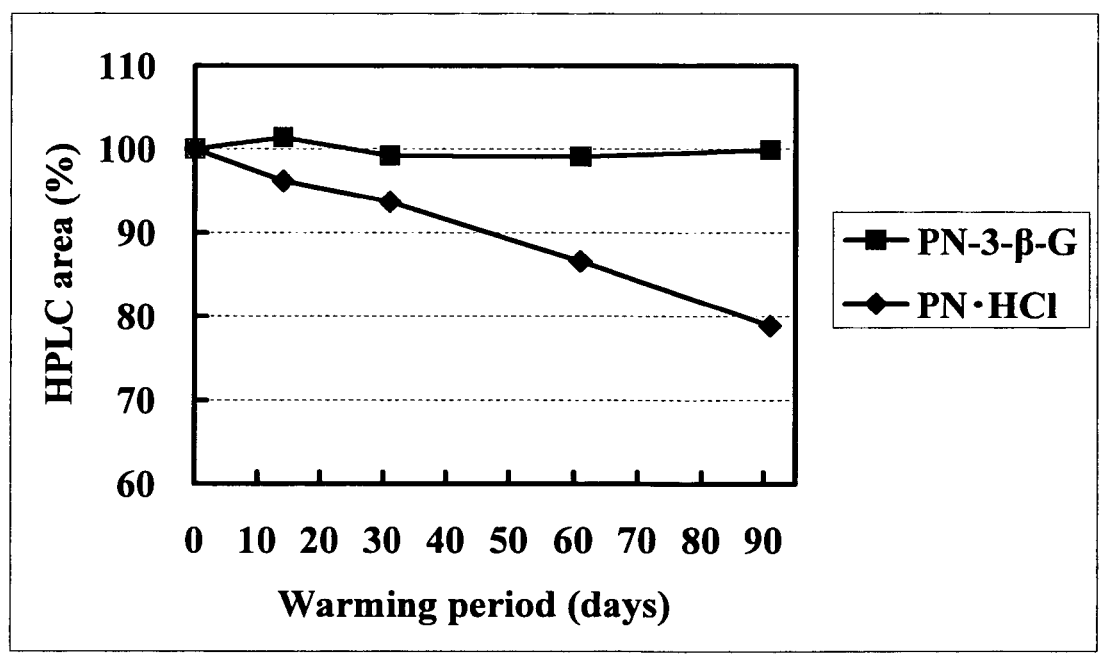
FIG. 2 shows thermal stability of the compound of the present invention. PN-3-β-G represents pyridoxine 3-β-D-glucoside, and PN.HCl represents pyridoxine hydrochloride.

The results are shown in FIG. 2. About 20% of pyridoxine hydrochloride was decomposed by warming at 50° C. for 90 days, whist almost no decomposition of pyridoxine 3-β-D-glucoside was observed. Moreover, the aqueous solution of pyridoxine hydrochloride colored in yellow after the warming at 50° C. for 90 days, whilst no coloring was observed for the aqueous solution of pyridoxine 3-β-D-glucoside.

Test Example 3

Figure 3:
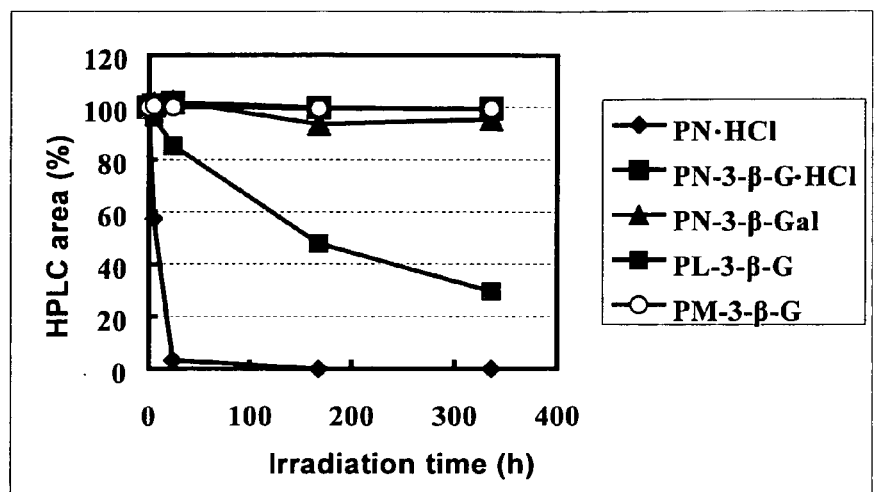
FIG. 3 shows light stability of the compounds of the present invention. PN-3-β-G.HCl represents pyridoxine 3-β-D-glucoside hydrochloride, PL-3-β-G represents pyridoxal 3-β-D-glucoside, PM-3-β-G represents pyridoxamine 3-β-D-glucoside, PN-3-β-Gal represents pyridoxine 3-β-D-galactoside, and PN.HCl represents pyridoxine hydrochloride.

Light Stability of Pyridoxine 3-β-D-glucoside Hydrochloride and Various 3-Glycosides Aqueous solutions (0.5% (w/v)) of pyridoxine 3-β-D-glucoside hydrochloride, pyridoxal 3-β-D-glucoside, pyridoxamine 3-β-D-glucoside, pyridoxine 3-β-D-galactoside, and pyridoxine hydrochloride (adjusted to pH 6.3 to 7.2 with HCl or NaOH) were each sealed in a volume of 0.3 ml in a 1-ml volume glass ampoule, and light irradiation and HPLC quantification were performed in the same manner as in Test Example 1. The results are shown in FIG. 3. Pyridoxine hydrochloride was almost completely decomposed in one day, whilst decomposition of pyridoxine 3-β-D-glucoside hydrochloride, pyridoxamine 3-β-D-glucoside and pyridoxine 3-β-D-galactoside was not observed even after the irradiation with the lamp for 14 days, and thus it was found that each light stability of these substances was remarkably improved. The light stability of pyridoxal 3-β-D-glucoside was also clearly improved. Moreover, the aqueous solution of pyridoxine hydrochloride colored in pale yellow after the light irradiation, whilst no coloring was observed for the aqueous solutions of pyridoxine 3-β-D-glucoside hydrochloride, pyridoxal 3-β-D-glucoside, pyridoxamine 3-β-D-glucoside, and pyridoxine 3-β-D-galactoside. Test Example 4 (thermal stability of pyridoxine 3-β-D-glucoside hydrochloride and various 3-glycosides)

Figure 4:
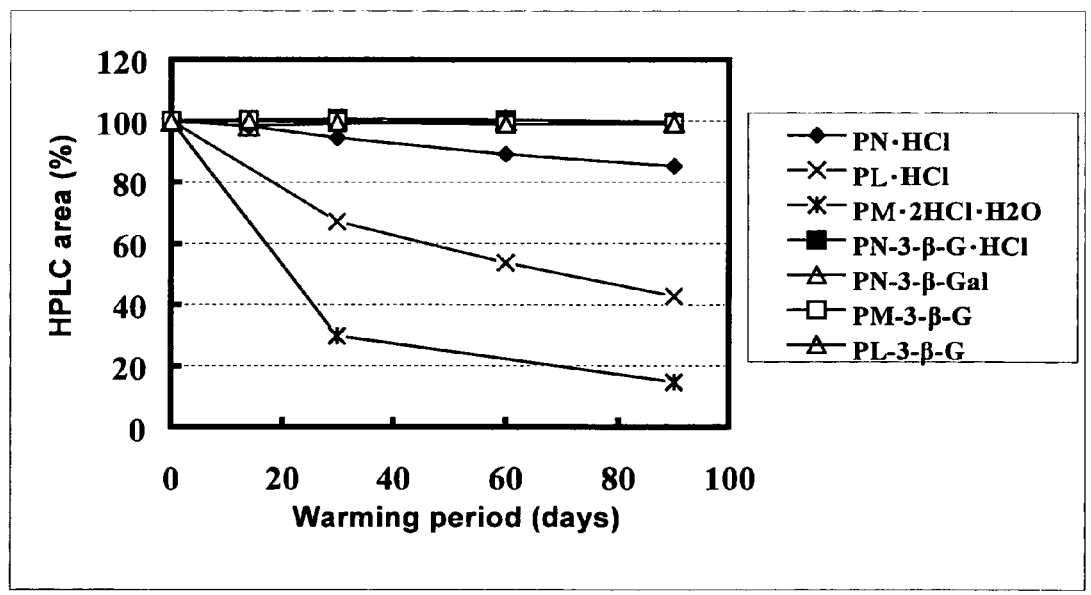
FIG. 4 shows thermal stability of the compounds of the present invention. PN-3-β-G.HCl represents pyridoxine 3-β-D-glucoside hydrochloride, PL-3-β-G represents pyridoxal 3-β-D-glucoside, PM-3-β-G represents pyridoxamine 3-β-D-glucoside, PN-3-β-Gal represents pyridoxine 3-β-D-galactoside, PN.HCl represents pyridoxine hydrochloride, PL.HCl represents pyridoxal hydrochloride, and PM.2HCl.H$_2$O represents pyridoxamine hydrochloride.

Aqueous solutions (0.5% (w/v)) of pyridoxine 3-β-D-glucoside hydrochloride, pyridoxal 3-β-D-glucoside, pyridoxamine 3-β-D-glucoside, pyridoxine 3-β-D-galactoside, pyridoxine hydrochloride, pyridoxal hydrochloride, and pyridoxamine hydrochloride (adjusted to pH 6.3 to 7.2 with HCl or NaOH) were each sealed in a volume of 0.3 ml in a 1-ml volume glass ampoule, and light irradiation and HPLC analysis were performed in the same manner as in Test Example 2. The results are shown in FIG. 4. About 15% of pyridoxine hydrochloride, 55% of pyridoxal hydrochloride, and 85% of pyridoxamine hydrochloride were decomposed by warming at 50° C. for 90 days, whilst almost no decomposition of each of pyridoxine 3-β-D-glucoside hydrochloride, pyridoxal 3-β-D-glucoside, pyridoxamine 3-α-D-glucoside, and pyridoxine 3-β-D-galactoside was observed. Moreover, the aqueous solutions of pyridoxine hydrochloride, pyridoxal hydrochloride, and pyridoxamine hydrochloride colored in yellow after the warming at 50° C. for 90 days, whilst no coloring was observed for the aqueous solutions of pyridoxine 3-β-D-glucoside hydrochloride, pyridoxal 3-β-D-glucoside, pyridoxamine 3-β-D-glucoside, and pyridoxine 3-β-D-galactoside.

Test Example 5

Light Stability of N-(4-pyridoxylmethylene)-L-serine 3-β-D-glucoside

Figure 5:
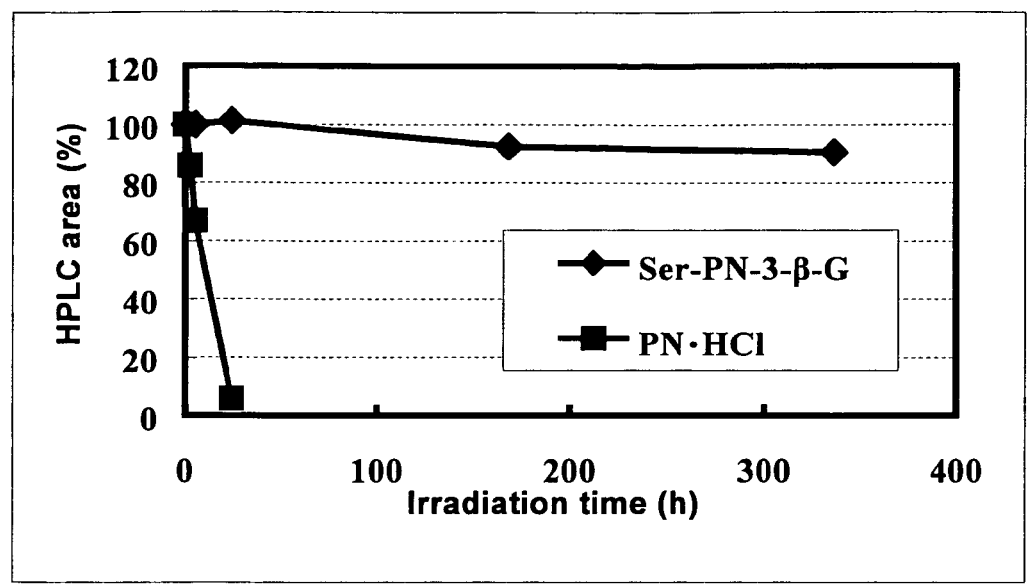
FIG. 5 shows light stability of the compound of the present invention. Ser-PN-3-β-G represents N-(4-pyridoxylmethylene)-L-serine 3-β-D-glucoside, and PN.HCl represents pyridoxine hydrochloride.

Aqueous solutions (0.5% (w/v)) of N-(4-pyridoxylmethylene)-L-serine 3-β-D-glucoside and pyridoxine hydrochloride (pH was adjusted with HCl or NaOH) were each sealed in a volume of 0.3 ml in a 1-ml volume glass ampoule, and light irradiation and HPLC quantification were performed in the same manner as in Test Example 1. The results are shown in FIG. 5. Pyridoxine hydrochloride was substantially decomposed in one day, whilst no decomposition was observed for N-(4-pyridoxylmethylene)-L-serine 3-α-D-glucoside even after the irradiation with the lamp for 14 days, and thus it was found that the light stability thereof was remarkably improved.

Test Example 6

Figure 6:
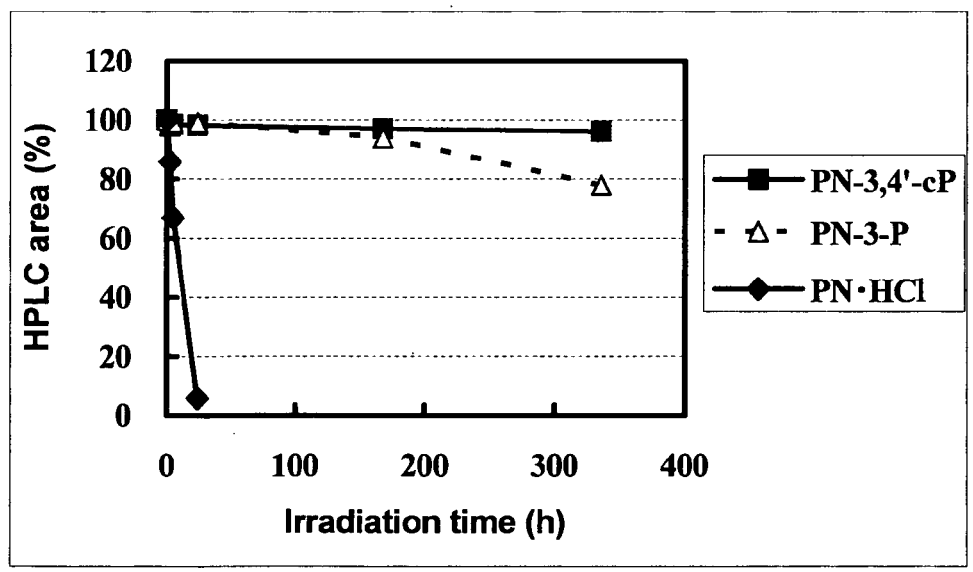
FIG. 6 shows light stability of the compounds of the present invention. PN-3,4'-cP represents pyridoxine 3,4'-cyclic sodium phosphate, PN-3-P represents pyridoxine 3-disodium phosphate, and PN.HCl represents pyridoxine hydrochloride.

Light Stability of Pyridoxine 3,4'-cyclic Sodium Phosphate and Pyridoxine 3-disodium phosphate Aqueous solutions (0.5% (w/v)) of pyridoxine 3,4'-cyclic sodium phosphate and pyridoxine 3-disodium phosphate (adjusted to pH 6.5 to 6.8) were each sealed in a volume of 0.3 ml in a 1-ml volume glass ampoule, and light irradiation and HPLC quantification were performed in the same manner as in Test Example 1. The results are shown in FIG. 6. Pyridoxine hydrochloride was substantially decomposed in one day, whilst no decomposition was observed for pyridoxine 3,4'-cyclic sodium phosphate even after the irradiation with the lamp for 14 days, and thus it was found that the light stability thereof was remarkably improved. The light stability of pyridoxine 3-disodium phosphate was also clearly improved. Moreover, the aqueous solution of pyridoxine hydrochloride was colored in pale yellow by the light irradiation, whilst the aqueous solutions of pyridoxine 3,4'-cyclic sodium phosphate and pyridoxine 3-disodium phosphate were not colored.

Test Example 7

Light Stability of Pyridoxine 3,4'-cyclic Magnesium Phosphate

Figure 7:
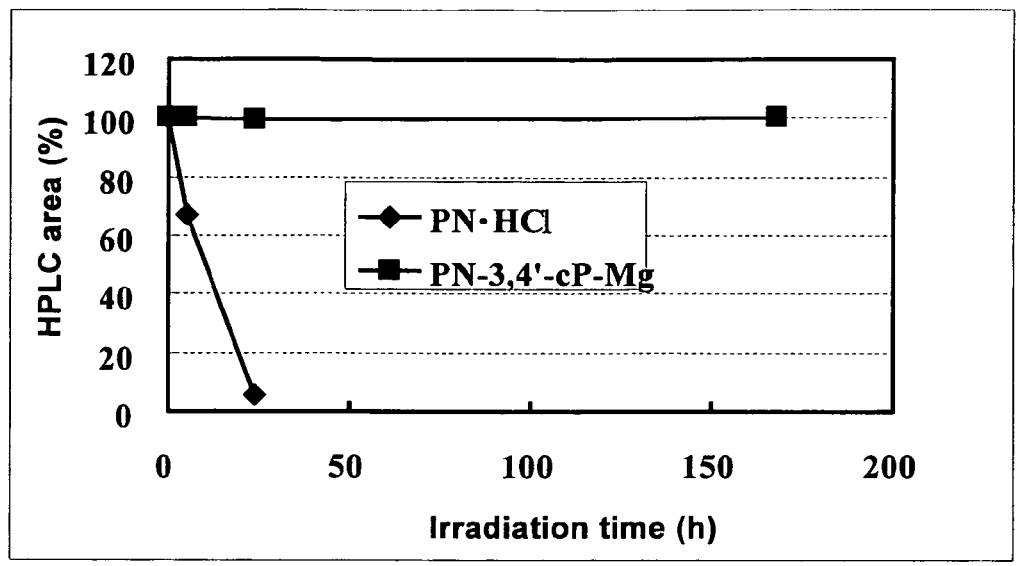
FIG. 7 shows light stability of the compound of the present invention. PN-3,4'-cP-Mg represents pyridoxine 3,4'-cyclic magnesium phosphate, and PN.HCl represents pyridoxine hydrochloride.

An aqueous solution (0.5% (w/v)) of pyridoxine 3,4-cyclic magnesium phosphate (adjusted to pH 6.5 to 6.8) was sealed in a volume of 0.3 ml in a 1-ml volume glass ampoule, and light irradiation for 7 days and HPLC quantification were performed in the same manner as in Test Example 1. The results are shown in FIG. 7.

Test Example 8

Light Stability of Pyridoxine 3-α-D-glucoside Aqueous Solution

Figure 8:
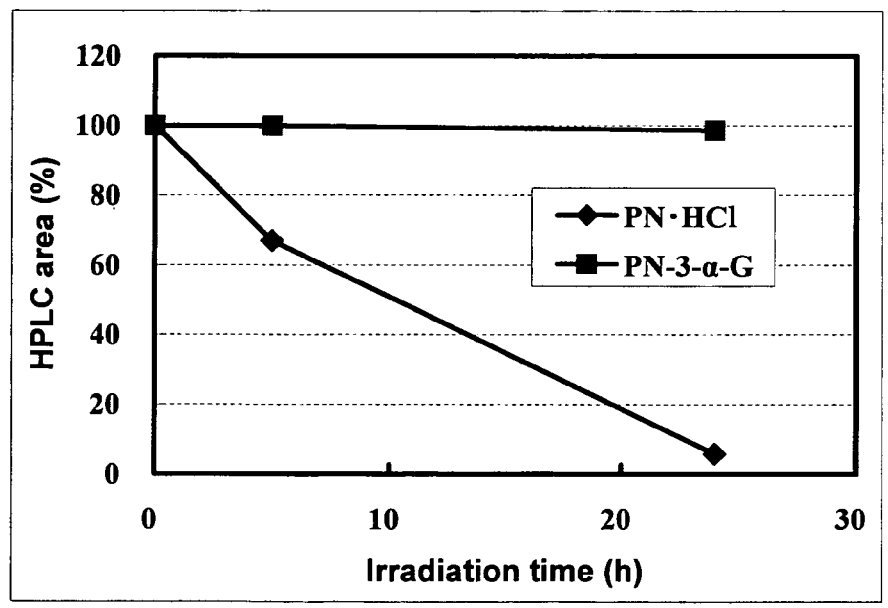
FIG. 8 shows light stability of the compound of the present invention. PN-3-α-G represents pyridoxine 3-α-D-glucoside, and PN.HCl represents pyridoxine hydrochloride.

An aqueous solution (0.5% (w/v)) of pyridoxine 3-α-D-glucoside (adjusted to pH 6.5 to 6.8) was sealed in a volume of 0.3 ml in a 1-ml volume glass ampoule, and light irradiation for 1 day and HPLC quantification were performed in the same manner as in Test Example 1. The results are shown in FIG. 8.

Test Example 9

Light Stability of Pyridoxine 3-sodium sulfate Formulated Agent

Figure 9:
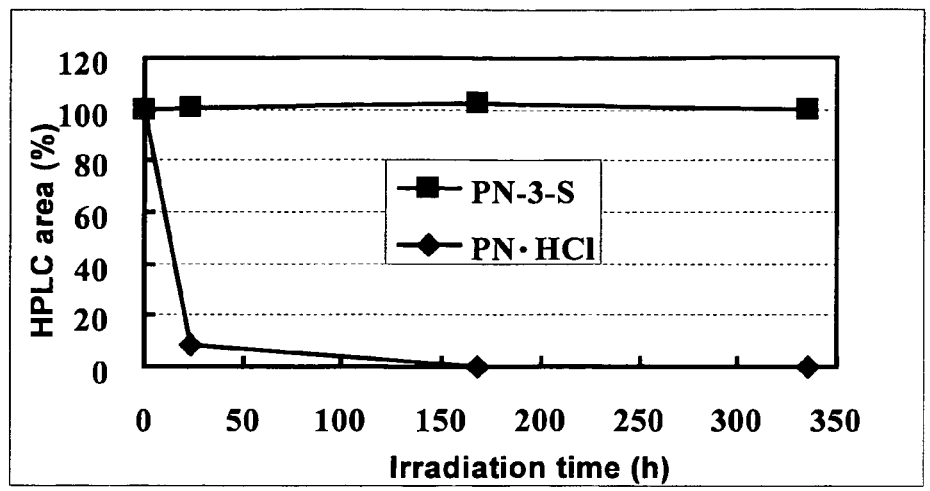
FIG. 9 shows light stability of the compound of the present invention. PN-3-S represents pyridoxine 3-sodium sulfate, and PN.HCl represents pyridoxine hydrochloride.

Pyridoxine 3-sodium sulfate was synthesized according to the method described in a literature (The Journal of Biological Chemistry, 262, pp. 2642-2644, 1987). An aqueous solution (0.5% (w/v)) of pyridoxine 3-sodium sulfate (adjusted to pH 6.5 to 6.8) was sealed in a volume of 0.3 ml in a 1-ml volume glass ampoule, and light irradiation for 14 days and HPLC quantification were performed in the same manner as in Test Example 1. The results are shown in FIG. 9.

Test Example 10

Thermal Stability of Pyridoxine 3,4'-cyclic Sodium Phosphate)

Figure 10:
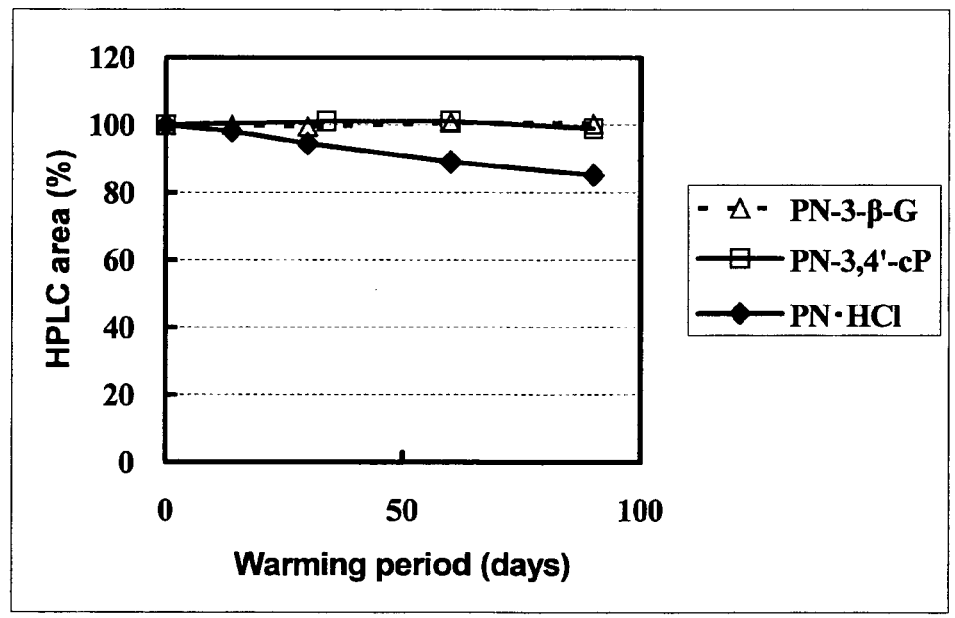
FIG. 10 shows thermal stability of the compounds of the present invention. PN-3-β-G represents pyridoxine 3-β-D- glucoside, PN-3,4'-cP represents pyridoxine 3,4'-cyclic sodium phosphate, and PN.HCl represents pyridoxine hydrochloride.

0.5% (w/v) Aqueous solutions of pyridoxine 3,4'-cyclic sodium phosphate and pyridoxine hydrochloride (adjusted to pH 6.5 to 6.8) were each sealed in a volume of 0.3 ml in a 1-ml volume glass ampoule, and warming at 50° C. and HPLC analysis were performed in the same manner as in Test Example 2. The results are shown in FIG. 10. About 15% of pyridoxine hydrochloride was decomposed by warming at 50° C. for 90 days, whilst almost no decomposition of pyridoxine 3,4-cyclic sodium phosphate was observed. Moreover, the aqueous solution of pyridoxine hydrochloride colored in yellow after the warming at 50° C. for 90 days, whilst no coloring was observed for the aqueous solution of pyridoxine 3,4-cyclic sodium phosphate.

Test Example 11

Lotion

Ceramide formulation (0.1 g), 1,3-butylene glycol (2.5 g), dipropylene glycol (2.5 g), and methylparaben (0.01 g) were warmed at 80° C. and stirred until the mixture became transparent. The mixture was cooled to 35° C., then added with 0.1 g of a vitamin B6 derivative (pyridoxine 3-β-D-glucoside, pyridoxine 3-β-D-glucoside hydrochloride, or pyridoxine 3,4-cyclic sodium phosphate: in Test Examples 11 to 16 mentioned below, the "vitamin B6 derivative" means one of these three kinds of substances) or 0.1 g of pyridoxine 3-sodium sulfate, 1.0 g of sorbitol-fermented polysaccharide and 90 ml of purified water with stirring, and the mixture were stirred until the added substances were dissolved. The solution was adjusted to pH 6.4 with 10% aqueous citric acid, and made into a volume of 100 ml with purified water to prepare a lotion. In this preparation, precipitates and the like were not observed. The prepared lotion in a volume of 6 ml was filled in a glass bottle, and exposed to light of a D65 fluorescent lamp at a total illumination of 0, 60,000, 180,000, or 300,000 lux·hr, and then the vitamin B6 derivative was quantified. The same sample was separately stored at 50° C., and after 0 day, 14 days, one month, and two months, the vitamin B6 derivative was quantified by the HPLC method described in Test Example 1.

The results obtained after the irradiation with the lamp are shown in FIG. 11. The remained pyridoxine hydrochloride was 42% after the irradiation at 180,000 lux·hr for 3 days, and 30% after the irradiation at 300,000 lux·hr for 5 days, and thus pyridoxine hydrochloride was almost completely decomposed. Whilst substantially no decomposition was observed for the vitamin B6 derivative even after the irradiation with the lamp for 5 days, and accordingly, the light stability thereof was found to be far more excellent.

The results obtained after the storage at 50° C. are shown in FIG. 12. Completely no decomposition or almost no decomposition of the vitamin B6 derivative was observed, and thus the thermal stability thereof was higher than that of pyridoxine hydrochloride.

Test Example 12

Shampoo

Sodium coconut oil fatty acid methyltaurine (10.0 g), polyoxyethylene alkyl ether sodium sulfate (20.0 g), lauryl dimethylaminoacetate betaine (10.0 g), coconut oil fatty acid diethanolamide (4.0 g), propylene glycol (2.0 g), vitamin B6 derivative (0.1 g), and methyl paraoxybenzoate (0.01 g) were added to purified water (40 ml), and warmed to 70° C. for dissolution. The solution was cooled to a temperature below 35° C., and then adjusted to pH 6.8 with 10% aqueous citric acid, and made into a volume of 100 ml with purified water to prepare a shampoo. In this preparation, precipitates and the like were not observed. The prepared shampoo in a volume of 6 ml was filled in a glass bottle, and exposed to light of a D65 fluorescent lamp at a total illumination of 0, 60,000, 180,000, or 300,000 lux·hr, and then the vitamin B6 derivative was quantified. The same sample was separately stored at 50° C., and after 0 day, 14 days, one month, and two months, the vitamin B6 derivative was quantified by the HPLC method in the same manner as in Test Example 11 mentioned above.

The results obtained after the irradiation with the lamp are shown in FIG. 13. Pyridoxine hydrochloride was decomposed in such degrees that the remained pyridoxine hydrochloride was 60% after the irradiation at 180,000 lux·hr for 3 days, and 58% after the irradiation at 300,000 lux·hr for 5 days. Whilst substantially no decomposition was observed for the vitamin B6 derivative even after the irradiation with the lamp for 5 days, and the light stability thereof was found to be far more excellent.

The results obtained after the storage at 50° C. are shown in FIG. 14. Completely no decomposition or almost no decomposition of the vitamin B6 derivative was observed, and thus the thermal stability thereof was higher than that of pyridoxine hydrochloride.

Example 13

Eye Lotion

Neostigmine methylsulfate (5 mg), potassium L-aspartate (0.4 g), boric acid (5 mg), sodium borate (5 mg), methyl paraoxybenzoate (10 mg), chlorobutanol (0.1 g), and vitamin B6 derivative (0.1 g) were dissolved in sterilized purified water (70 ml). After dissolution, the solution was made into a volume of 100 ml with sterilized purified water to prepare an eye lotion. In this preparation, precipitates and the like were not observed. The prepared eye lotion in a volume of 6 ml was put into a glass bottle, and exposed to light of a D65 fluorescent lamp at a total illumination of 0, 60,000, 180,000, or 300,000 lux·hr, and then the vitamin B6 derivative was quantified by the HPLC method in the same manner as in Test Example 11 mentioned above.

The results obtained after the irradiation with the lamp are shown in FIG. 15. Pyridoxine hydrochloride was decomposed in such degrees that the remained pyridoxine hydrochloride was 68% after the irradiation at 180,000 lux·hr for 3 days, and 49% after the irradiation at 300,000 lux·hr for 5 days. Whilst substantially no decomposition was observed for the vitamin B6 derivative even after the irradiation with the lamp for 5 days, and the light stability thereof was found to be far more excellent.

Example 14

Drinking Water

Glucose (4.6 g), Aspartame (0.01 g), citric acid (0.1 g), sodium chloride (0.02 g), potassium chloride (0.02 g), magnesium chloride (0.01 g), calcium lactate (0.04 g), vitamin B6 derivative (0.01 g), sodium L-aspartate (0.07 g), sodium L-glutamate (0.02 g), L-arginine (0.02 g), and aromatic (0.1 g) were dissolved in purified water (70 ml), and then made into a volume of 100 ml with purified water to prepare a drinking water. In this preparation, precipitates and the like were not observed. The prepared drinking water in a volume of 6 ml was filled in a glass bottle, and exposed to light of a D65 fluorescent lamp at a total illumination of 0, 60,000, 180,000, or 300,000 lux·hr, and then the vitamin B6 derivative was quantified by the HPLC method in the same manner as in Test Example 1.

The results obtained after the irradiation with the lamp are shown in FIG. 16. Pyridoxine hydrochloride was decomposed in such degrees that the remained pyridoxine hydrochloride was 68% after the irradiation at 180,000 lux·hr for 3 days, and 56% after the irradiation at 300,000 lux·hr for 5 days. Whilst substantially no decomposition was observed for the vitamin B6 derivative even after the irradiation with the lamp for 5 days, and the light stability thereof was found to be far more excellent.

Example 15

Dog Food

A vitamin B6 derivative (0.1 g) was added to wheat flour (10 g), and uniformly mixed. The mixture was further successively added with breast meat of chicken (40.0 g), soybean protein (30.0 g), glucose (5.0 g), citric acid (0.001 g), sodium chloride (1.0 g), copper sulfate (0.01 g), iron sulfate (0.01 g), sorbic acid (0.3 g), and propylene glycol (5.0 g), and uniformly mixed. The mixture was made 100 g with purified water, and uniformly mixed to prepare dog food.

The prepared dog food in an amount of 5 g was put into a petri dish, and exposed to light of a D65 fluorescent lamp at a total illumination of 0, 60,000, 180,000, or 300,000 lux·hr, and then the vitamin B6 derivative was quantified by the HPLC method in the same manner as in Test Example 11 mentioned above.

The results obtained after the irradiation with the lamp are shown in FIG. 17. Pyridoxine hydrochloride was decomposed in such degrees that the remained pyridoxine hydrochloride was 90% after the irradiation at 180,000 lux·hr for 3 days, and 85% after the irradiation at 300,000 lux·hr for 5 days. Whilst substantially no decomposition was observed for the vitamin B6 derivative even after the irradiation with the lamp for 5 days, and the light stability thereof was found to be far more excellent.

Example 16

Test for Change in Formulation

Calcium pantothenate (1 g) and a vitamin B6 derivative (1 g) was uniformly mixed in a mortar to prepare a sample in the form of a powder for stability test. The sample placed in an opened glass bottle was stored in an oven at 40° C. under 75% humidity. Appearance of the sample was examined by visual inspection after 0 day, 14 days, and one month, and the vitamin B6 derivative and calcium pantothenate were quantified by the HPLC method in the same manner as in Test Example 11 mentioned above, provided that the detection wavelength for calcium pantothenate was 210 nm.

The change in the formulation is shown in FIG. 18. As for the formulation with pyridoxine hydrochloride, the remained calcium pantothenate was 81%, the white appearance became brown, and blocking and deliquescence were observed after the storage at 40° C. and 75% humidity for one month. As for the formulation with the vitamin B6 derivative, substantially no decomposition of the formulation was observed, and thus improvement of the stability in the formulation was confirmed.

Calcium pantothenate (0.1 g) and a vitamin B6 derivative (0.1 g) were dissolved in purified water and made 100 ml to prepare a sample for stability test in the form of a solution. The sample filled in a sealed glass bottle was stored at 40° C. Appearance of the sample was examined by visual inspection after 0 day, 14 days, and one month, and the vitamin B6 derivative and calcium pantothenate were quantified by the HPLC method in the same manner as in Test Example 11 mentioned above, provided that the detection wavelength for calcium pantothenate was 210 nm.

The change in the formulation is shown in FIG. 19. As for the formulation with pyridoxine hydrochloride, the remained calcium pantothenate was 83% after the storage at 40° C. for one month. As for the formulation with the vitamin B6 derivative, substantially no decomposition of the formulation was observed, and thus improvement of the stability in the formulation was confirmed.

Test Example 17

Test for Melanin Production Suppression and Cell Survival Rate in Cultured Cells Cultured mouse B16 melanoma cells were used. An appropriate amount of MEM medium containing 10% FBS was added to wells of two 6-well plates, and the B16 melanoma cells were inoculated, and incubated at 37° C. with 5 volume % $CO_2$. On the next day, a sample-containing solution was added so that the medium contained the vitamin B6 derivative (pyridoxine 3-β-D-glucoside or pyridoxine 3-β-D-glucoside hydrochloride) at a final solid concentrations shown in FIG. 20, and then mixed. On the 5th day of the culture, the medium was exchanged, and the sample-containing solution was again added. On the next day, the medium was removed, and for one plate, the cells were washed with phosphate buffer (pH 7.0), and then collected. Then, whitening degree of the cultured B16 melanoma cells was evaluated according to the criteria mentioned below by using 100 μg/ml kojic acid as a control. The results are shown in the following tables. In the tables, + means "whitening effect comparable to that of the control", ± means "whitening effect a little weaker than that of the control", × means "no effect", and "–" means that test was not performed. The cell growth rate is indicated with a relative ratio based on that of the control, which is taken as 100%.

| PN-3-β-G | | | | | | | |
|---|---|---|---|---|---|---|---|
| Final concentration (μg/mL) | 0 | 10 | 30 | 100 | 300 | 1000 | – |
| Evaluation | × | × | × | × | ± | + | – |
| Cell growth rate (%) | 100 | 101 | 101 | 101 | 101 | 102 | – |

| PN-3-β-G-HCl | | | | | | | |
|---|---|---|---|---|---|---|---|
| Final concentration (μg/mL) | 0 | – | – | 100 | 333.3 | 1000 | 3333 |
| Evaluation | × | – | – | × | × | × | + |
| Cell growth rate (%) | 100 | – | – | 100 | 100 | 97 | 87 |

From the results shown in the tables, it is clearly understood that the vitamin B6 derivatives (pyridoxine 3-β-D-glucoside and pyridoxine 3-β-D-glucoside hydrochloride) exhibited superior suppressing effect on melanin production.

Test Example 18

Test for Evaluating Melanin Production Suppression by Combination with Whitening Agent Cultured mouse B16 melanoma cells were used. A vitamin B6 derivative (pyridoxine 3-β-D-glucoside) and arbutin (Wako Pure Chemical Industries) dissolved in purified water at given concentrations were each added to the medium at a concentration of 100 μM. With exchanges of the medium during the culture, the cells were cultured for 5 days, and then collected. The cell number was counted, and then intracellular melanin was quantified. As a control added with a solvent, the medium added with purified water was used. Based on the amount of the melanin observed for the control added with the solvent, which was taken as 1, the relative amount of intracellular melanin observed for each sample concentration was considered a melanin production ratio. The results are shown in FIG. 20.

It was demonstrated that the vitamin B6 derivative (pyridoxine 3-β-D-glucoside) combined with the other whitening ingredient exhibited superior suppressing effect on melanin production. From the results mentioned above, it was concluded that the vitamin B6 derivative successfully exhibits more excellent whitening effect by combination with another whitening ingredient.

Test Example 19

Test for Dermatopathy Caused by Ultraviolet Irradiation in Hairless Mouse

It was evaluated whether or not the sample prepared by the following preparing method suppressed wrinkle formation caused by ultraviolet irradiation.

[Preparation of Sample (Anti-Dermatopathy Preparation)]

Pyridoxine 3-β-D-glucoside hydrochloride and pentasodium diethylenetriaminepentaacetate (DETAPAC) solution were each dissolved in a base (polyethylene glycol 1000:ethyl alcohol=1:1) to prepare samples at a concentration of 2%, and the samples were used for the skin evaluation test using ultraviolet irradiation on hairless mice. DETAPAC was used as a positive control.

[Sample Application Method and Ultraviolet Irradiation Method]

Mice (10-week old) in each group consisting of 8 mice were applied with each of the aforementioned samples on the back 90 minutes before ultraviolet irradiation, and irradiated with ultraviolet rays of a fixed quantity (Toshiba FL20 S-BLB lamp) for 2 hours (5 times/week) over ten weeks to examine suppressing effect on wrinkle formation.

Ultraviolet absorption spectra of the samples were measured to confirm that the samples had no influence on the evaluation test.

[Evaluation Method]
(Suppressing Effect on Wrinkle Formation)

Wrinkle formation after the ultraviolet irradiation of ten weeks was graded in accordance with the "skin photoaging grades" mentioned below. The results were indicated as averages of the scores for eight mice. The test and evaluation methods used were modified from those described in the article by Bissett et al. (Photochem. Photobiol., Volume: 46, Issue: 3, Page: 367-78, Year 1987).

| \<Skin photoaging grades\> | |
|---|---|
| Score | Conditions |
| 0 | (1) Fine lines are vertically formed. |
|   | (2) Skin color is pink. |
| 1 | (1) Fine lines decreases. |
| 2 | (1) Fine lines disappear. |
|   | (2) Fine wrinkles are formed. |
|   | (3) Bags begin to be formed. |
| 3 | (1) Shallow wrinkles are formed. |
|   | (2) Skin color begins to be dulled from pink. |
| 4 | (1) Deep wrinkles are formed. |
|   | (2) Scleroderma begins to develop. |
|   | (3) Skin elasticity decreases. |
| 5 | (1) Deep wrinkles increase. |
|   | (2) Bags increase. |
|   | (3) Skin color is xanthosis. |
| 6 | (1) Tumor is induced. |
|   | (2) Skin elasticity is completely lost. |
| 7 | (1) Number of tumors increases. |
|   | (2) Pachymenia is aggravated. |

As clearly indicated from the results shown in FIG. 21, the vitamin B6 derivative (pyridoxine 3-β-D-glucoside hydrochloride) exhibited suppressing effect on wrinkle formation comparable to or higher than that of DETAPAC used as the positive control. DETAPAC has an iron chelating ability as described in the report of Graf et al. (J. Biol. Chem., 259(6), pp. 3620-4, 1984), and an iron chelator is recognized to suppress wrinkles and be involved in dermatopathy caused by ultraviolet irradiation as demonstrated in the report of Jurkiewicz et al. (Photochem. Photobiol, 59, pp. 1-4, 1994).

Test Example 20

Skin Lotion

A solution obtained by mixing and dissolving the following ingredients (3) to (5), and (9) to (11) and a solution obtained by mixing and dissolving the following ingredients (1), (2), (6) to (8), and (12) were uniformly mixed to obtain a skin lotion.

| (Formulation) | (%) |
|---|---|
| (1) Glycerol | 5.0 |
| (2) 1,3-Butylene glycol | 6.5 |
| (3) Polyoxyethylene (20 E.O.) sorbitan monolaurate | 1.2 |
| (4) Ethyl alcohol | 8.0 |
| (5) Vitamin B6 derivative (pyridoxine 3-β-D-glucoside) | 0.001 |
| (6) L-Ascorbic acid glucoside | 0.5 |
| (7) Lactic acid | 0.05 |
| (8) Sodium lactate | 0.1 |
| (9) 2-Ethylhexyl paramethoxycinnamate | 3.0 |
| (10) Preservative | Sufficient quantity |
| (11) Aromatic | Sufficient quantity |
| (12) Purified water | Residual quantity |

The skin lotion prepared in Test Example 20 was a superior cosmetic that achieved smoothing and whitening of the skin upon dermal application. Precipitates and the like were not observed in this skin lotion, and the stability was also favorable.

Test Example 21

Milky Lotion

A mixture obtained by mixing the following ingredients (13), (16), and (18) with heating and kept at 70° C. was added to a mixture obtained by mixing the following ingredients (1) to (9), (12), and (15) with heating and kept at 70° C., mixed, and uniformly emulsified. This emulsion was cooled, then further added with the ingredients (10) and (11), and uniformly mixed. This mixture was added with the ingredient (14), sufficiently stirred, added with the ingredient (17), and uniformly mixed to obtain a milky lotion.

| (Formulation) | (%) |
|---|---|
| (1) Polyoxyethylene (10 E.O.) sorbitan monostearate | 1.0 |
| (2) Polyoxyethylene (60 E.O.) sorbit tetraoleate | 0.5 |
| (3) Glyceryl monostearate | 1.0 |
| (4) Stearic acid | 0.5 |
| (5) Behenyl alcohol | 0.5 |
| (6) Squalane | 8.0 |
| (7) Retinol palmitate *1 | 0.002 |
| (8) Dipottasium glycyrrhizinate *2 | 0.3 |
| (9) Vitamin B6 derivative (pyridoxine 3-β-D-glucoside) | 0.01 |
| (10) Licorice extract *3 | 0.1 |
| (11) Hyaluronic acid | 0.1 |
| (12) Preservative | 0.1 |
| (13) Carboxyvinyl polymer | 0.1 |
| (14) Sodium hydroxide | 0.05 |
| (15) Ethyl alcohol | 5.0 |
| (16) Purified water | Residual quantity |

| (Formulation) | (%) |
|---|---|
| (17) Aromatic | Sufficient quantity |
| (18) Zinc oxide *4 | 5.0 |

*1 Nippon Roche
*2 Maruzen Pharmaceuticals
*3 Maruzen Pharmaceuticals
*4 Sigma

The milky lotion prepared in Test Example 21 was a superior cosmetic that achieved smoothing and whitening of the skin upon dermal application. Precipitates and the like were not observed in this milky lotion, and the stability was also favorable.

INDUSTRIAL APPLICABILITY

The compounds of the present invention represented by the general formula (I) are characterized by superior stability, especially remarkably improved light stability. The compounds of the present invention represented by the general formula (I) can be efficiently prepared at low cost by using a compound represented by the general formula (IV) of the present invention as a synthetic intermediate. In the compositions of the present invention, the thermal stability and light stability of vitamin B6 derivatives and other vitamins are remarkably improved, and reduction in the contents of the aforementioned active ingredients after long term storage or distribution processes decreases. Moreover, the compositions of the present invention can exhibit superior whitening effect, anti-aging effect, and effect of suppressing wrinkle formation by exposure to ultraviolet light.

What is claimed is:

1. A compound represented by the following general formula (I) or a salt thereof:

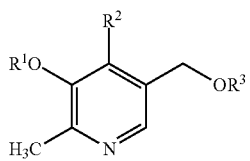
(I)

wherein $R^1$ represents a cyclic phosphate group bound to $R^2$; $R^2$ represents —$CH_2OH$, —CHO, —$CH_2NH_2$, —$CH_2$-amino acid residue, or —$CH_2$—$OPO_2H$; and $R^3$ represents a hydrogen atom, or —$PO_3H_2$.

2. The compound or a salt thereof according to claim 1, which is pyridoxine 3,4'-cyclic phosphate or a salt thereof.

3. A compound represented by the following general formula (IV) or a salt thereof:

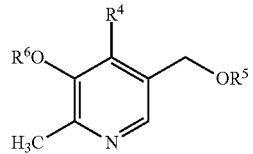
(IV)

wherein $R^4$ represents —$CH_2OH$, —CHO, or —$CH_2NH_2$, or represents —$CH_2OH$, —CHO, or —$CH_2NH_2$ protected with a protective group; $R^5$ represents a hydrogen atom, a protective group of hydroxyl group, a phosphate group, or a protected phosphate group; and $R^6$ represents a cyclic phosphate group bound to $R^4$ which may have a protective group.

4. A composition for a cosmetic, a medicament, a foodstuff, and/or a feed comprising a compound represented by the following general formula (V) or a salt thereof:

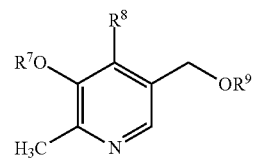
(V)

wherein $R^7$ represents a cyclic phosphate group bound to $R^8$; $R^8$ represents —$CH_2OH$, —CHO, —$CH_2NH_2$, —$CH_2$-amino acid residue, or —$CH_2$—$OPO_2H$; and $R^9$ represents a hydrogen atom, or —$PO_3H_2$.

5. A method for stabilizing calcium pantothenate contained in a cosmetic, a medicament, a foodstuff, and/or a feed from thermal decomposition and decomposition initiated by U.V. light by adding a compound represented by the general formula (V) or a salt thereof mentioned in claim 4 to the cosmetic, the medicament, the foodstuff, and/or the feed.

6. A composition for a cosmetic, a medicament, foodstuff, and/or a feed containing a compound represented by the general formula (V) or a salt thereof mentioned in claim 4 and at least one kind of vitamin, wherein stability of the vitamin is improved.

7. A composition comprising (A) a compound represented by the general formula (V) according to claim 4, and (B) one or more kinds of substances selected from the group consisting of a whitening agent, an antioxidant, an antiphlogistic, a circulation accelerator, a cell activation agent, and an ultraviolet absorber, which is used as a whitening agent, an anti-aging agent, and/or an agent for suppressing wrinkle formation by exposure to ultraviolet light.

8. A whitening agent containing (A) a compound represented by the general formula (V) mentioned in claim 4, and (B) arbutin.

* * * * *